United States Patent
Kerschbaumer et al.

(10) Patent No.: US 9,465,037 B2
(45) Date of Patent: Oct. 11, 2016

(54) CHARACTERIZATION OF CHO-MIF GENE AND PROTEIN, AND USE THEREOF

(71) Applicants: Baxalta GmbH, Glattpark (Opfikon) (CH); Baxalta Incorporated, Bannockburn, IL (US)

(72) Inventors: Randolf J. Kerschbaumer, Klosterneuburg (AT); Dirk Voelkel, Vienna (AT); Gerhard Antoine, Gross-Enzersdorf (AT); Friedrich Scheiflinger, Vienna (AT); Geert C. Mudde, Breitenfurt (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/350,187

(22) PCT Filed: Oct. 4, 2012

(86) PCT No.: PCT/EP2012/069602
§ 371 (c)(1),
(2) Date: Apr. 7, 2014

(87) PCT Pub. No.: WO2013/050457
PCT Pub. Date: Apr. 11, 2013

(65) Prior Publication Data
US 2014/0287443 A1    Sep. 25, 2014

Related U.S. Application Data

(60) Provisional application No. 61/545,047, filed on Oct. 7, 2011.

(51) Int. Cl.
| | | |
|---|---|---|
| C12N 5/10 | (2006.01) | |
| C12N 5/16 | (2006.01) | |
| C12N 15/12 | (2006.01) | |
| C12N 15/63 | (2006.01) | |
| G01N 33/53 | (2006.01) | |
| G01N 33/68 | (2006.01) | |
| C07K 16/24 | (2006.01) | |

(52) U.S. Cl.
CPC ........... *G01N 33/6863* (2013.01); *C07K 16/24* (2013.01); *G01N 33/6854* (2013.01); *G01N 2333/52* (2013.01)

(58) Field of Classification Search
None
See application file for complete search history.

(56) References Cited

U.S. PATENT DOCUMENTS

| 6,030,615 A | 2/2000 | Bucala et al. |
| 6,645,493 B1 | 11/2003 | Bucala et al. |
| 2003/0235584 A1 | 12/2003 | Kloetzer et al. |

FOREIGN PATENT DOCUMENTS

| WO | WO 01/64749 A2 | 9/2001 |
| WO | WO 01/64749 A3 | 9/2001 |
| WO | WO 2009/086920 A1 | 7/2009 |

OTHER PUBLICATIONS

Baugh, J.A. et al., "Macrophage migration inhibitory factor," *Crit Care Med*, 2002, vol. 30, No. 1 (Suppl.), pp. S27-S35.
Bloom, B.R. et al., "Mechanism of a Reaction in Vitro Associated with Delayed-Type Hypersensitivity," *Science*, Apr. 11, 1966, vol. 153, pp. 80-82.
Calandra, T. et al., "MIF as a glucocorticoid-induced modulator of cytokine production," *Nature*, Sep. 7, 1995, vol. 377, pp. 68-71.
Calandra, T. et al., "Macrophage Migration Inhibitory Factor: A Counter-Regulator of Glucocorticoid Action and Critical Mediator of Septic Shock," *Journal of Inflammation*, 1996, vol. 47, pp. 39-51.
David, J. R., "Delayed Hypersensitive in Vitro: Its Mediation by Cell-Free Substances Formed by Lymphoid Cell-Antigen Interaction," *Proc. Natl. Acad. Sci.*, 1966, vol. 56, pp. 72-77.
Galat, A. et al., "A diversified family of 12-kDa proteins with a high amino acid sequence similarity to macrophage migration-inhibitory factor (MIF)," *Eur. J. Biochem.*, 1994, vol. 224, pp. 417-421.
International Search Report for International Patent Application No. PCT/EP2012/069602 mailed Feb. 5, 2013, 4 pages.
Lue, H. et al., "Macrophage migration inhibitory factor (MIF) promotes cell survival by activation of the Akt pathway and role for CSN5/JAB1 in the control of autocrine MIF activity," *Oncogene*, 2007, vol. 26, p. 5046-5059.
Mitchell, R.A. et al., "Mechanisms and effectors of MIF-dependent promotion of tumourigenesis," *Cellular Signalling*, 2004, vol. 16, pp. 13-19.
Nishihira, J., "Macrophage Migration Inhibitory Factor (MIF): Its Essential Role in the Immune System and Cell Growth," *Journal of Interferon and Cytokine Research*, 2000, vol. 20, pp. 751-762.
Shimizu, T. et al., "Identification of macrophage migration inhibitory factor (MIF) in human skin and its immunohistochemical localization," *FEBS Letters*, 1996, vol. 381, pp. 199-202.
Sun, H-W. et al., "Crystal structure at 2.6-Å resolution of human macrophage migration inhibitory factor," *Proc. Natl. Acad. Sci. USA*, May 1996, vol. 93, pp. 5191-5196.
Watarai, H. et al., "Posttranslational modification of the glycosylation inhibiting factor (GIF) gene product generates bioactive GIF," *PNAS*, Nov. 21, 2000, vol. 97, No. 24, pp. 13251-1325.
Weiser, W.Y. et al., "Molecular cloning of a cDNA encoding a human macrophage migration inhibitory factor," *Proc. Natl. Acad. Sci. USA*, Oct. 1989, vol. 86, pp. 7522-7526.

*Primary Examiner* — Elizabeth C Kemmerer
(74) *Attorney, Agent, or Firm* — Morgan, Lewis & Bockius LLP

(57) ABSTRACT

The present invention is concerned with the specific and highly sensitive detection of specific CHO-MIF (macrophage migration inhibitory factor from Chinese Ovarian Hamster cell line) complexes in the production of anti-MIF antibodies. The present invention is further concerned with the provision of specific antibodies which can be used for a CHO-MIF detection method. The present invention is also concerned with a CHO MIF knockout cell line and use thereof. The present invention also provides preparations obtained from recombinant production in CHO cell lines which are essentially free of CHO-MIF.

29 Claims, 13 Drawing Sheets

Figure 1

Every bloc contains:
Lane 1 number of amino acid
Lane 2 protein sequence
Lane 3 DNA sequence
Lane 4 number of nucleotide (SEQ ID NO: 1)

```
Nr. AA    01  02  03  04  05  06  07  08  09  10  11  12  13  14  15  16
protein   M   P   M   F   T   V   N   T   N   V   P   R   A   S   V   P
DNA       ATG CCG ATG TTC ACC GTG AAC ACC AAC GTT CCC CGC GCC TCC GTG CCA
Nr.base           9           18          27          36          45

17  18  19  20  21  22  23  24  25  26  27  28  29  30  31  32  33  34
          E   G   L   L   S   E   L   T   Q   Q   L   A   Q   A   T   G   K   P
          GAG GGG CTT CTC TCC GAG CTC ACC CAG CAG CTG GCG CAG GCC ACC GGC AAG CCG
                      57          66          75          84          93          102

35  36  37  38  39  40  41  42  43  44  45  46  47  48  49  50  51  52
          A   Q   Y   I   A   V   H   V   V   P   D   Q   L   M   T   F   S   G
          GCC CAG TAC ATC GCA GTG CAC GTG GTC CCG GAC CAG CTC ATG ACT TTT AGC GGC
                      111         120         129         138         147         156

53  54  55  56  57  58  59  60  61  62  63  64  65  66  67  68  69  70
          S   S   D   P   C   A   L   C   S   L   H   S   I   G   K   I   G   G
          TCT AGC GAC CCC TGC GCC CTG TGC AGC CTG CAT AGT ATC GGC AAG ATC GGC GGC
                      165         174         183         192         201         210

71  72  73  74  75  76  77  78  79  80  81  82  83  84  85  86  87  88
          A   Q   N   R   T   Y   S   K   L   L   C   G   L   L   A   D   R   L
          GCG CAG AAC CGC ACC TAC AGC AAG CTG CTG TGC GGC CTG CTG GCT GAT CGC CTG
                      219         228         237         246         255         264

89  90  91  92  93  94  95  96  97  98  99  100 101 102 103 104 105 106
          H   I   S   P   D   R   I   Y   I   N   Y   Y   D   M   S   A   A   N
          CAC ATC AGC CCG GAC CGG ATC TAC ATC AAT TAT TAC GAC ATG AGC GCG GCC AAC
                      273         282         291         300         309         318

107 108 109 110 111 112 113 114 115
          V   G   W   N   G   S   T   F   A   STOP
          GTG GGC TGG AAC GGC TCC ACC TTC GCT TGA
                      327         336         345
```

Figure 2

```
           --EXON 1--  --EXON 1--  --EXON 1--  --EXON 1--  --EXON 1--  --EXON 1--
gDNA->     TTGGGCCACA  TCCCGCGTCG  CACTGTCCTC  TACTCCCCGC  TTGCAGTCCC  CTCCGCCACC

--EXON 1--  --EXON 1--  --EXON 1--  --EXON 1--  --EXON 1--  --EXON 1--
gDNA->     ATGCCGATGT  TCACCGTGAA  CACCAACGTT  CCCCGCGCCT  CCGTGCCAGA  GGGGCTTCTC   60
cDNA->     ATGCCGATGT  TCACCGTGAA  CACCAACGTT  CCCCGCGCCT  CCGTGCCAGA  GGGGCTTCTC
Protein     M  P  M     F  T  V  N    T  N  V    P  R  A     S  V  P  E   G  L  L
           I->Translation start --EXON 1--  --EXON 1--  --EXON 1--  --EXON 1--  --EXON 1--
gDNA->     TCCGAGCTCA  CCCAGCAGCT  GGCGCAGGCC  ACCGGCAAGC  CGGCCCAGGT  TTGCAGGGAG  120
cDNA->     TCCGAGCTCA  CCCAGCAGCT  GGCGCAGGCC  ACCGGCAAGC  CGGCCCAG--  ----------
Protein     S  E  L     T  Q  Q  L    A  Q  A    T  G  K     P  A  Q gDNA->     GGTACAGGAA  GAGAGAGAGT  GGGGAGGGAG  GGCCCGTGCG  CCCGGCCGCC  GGGCAGAGGA  180
cDNA->     ----------  ----------  ----------  ----------  ----------  ---------- gDNA->     AGAATGGGGA  TGGGAACCGC  GGCGGGCGGC  TGGAGGGCTG  GAGGCTGGAG  CTCCCCGGAG  240
cDNA->     ----------  ----------  ----------  ----------  ----------  ---------- gDNA->     CCCTGTGGCC  CCGTGGTCTT  TCAGGCGGGC  TAACCGCGCG  TCCACCCCTC  CCCCGCAGTA  300
cDNA->     ----------  ----------  ----------  ----------  ----------  -------TA
Protein                                                                         Y --EXON 2--  --EXON 2--  --EXON 2--  --EXON 2--  --EXON 2--  --EXON 2--
gDNA->     CATCGCAGTG  CACGTGGTCC  CGGACCAGCT  CATGACTTTT  AGCGGCTCTA  GCGACCCCTG  360
cDNA->     CATCGCAGTG  CACGTGGTCC  CGGACCAGCT  CATGACTTTT  AGCGGCTCTA  GCGACCCCTG
Protein     I  A  V     H  V  V     P  D  Q  L    M  T  F    S  G  S     S  D  P  C --EXON 2--  --EXON 2--  --EXON 2--  --EXON 2--  --EXON 2--  --EXON 2--
gDNA->     CGCCCTGTGC  AGCCTGCATA  GTATCGGCAA  GATCGGCGGC  GCGCAGAACC  GCACCTACAG  420
cDNA->     CGCCCTGTGC  AGCCTGCATA  GTATCGGCAA  GATCGGCGGC  GCGCAGAACC  GCACCTACAG
Protein     A  L  C    S  L  H     S  I  G  K    I  G  G    A  Q  N     R  T  Y  S --EXON 2--  --EXON 2--  --EXON 2--  --EXON 2--  --EXON 2--
gDNA->     CAAGCTGCTG  TGCGGCCTGC  TGGCTGATCG  CCTGCACATC  AGCCCCGGACC  GGTGCGTGGG  480
cDNA->     CAAGCTGCTG  TGCGGCCTGC  TGGCTGATCG  CCTGCACATC  AGCCCCGGACC  GG--------
Protein     K  L  L    C  G  L     L  A  D  R    L  H  I     S  P  D  R gDNA->     GGTGGGGTGG  GGTGAGGGGC  GCTGGGAGGT  GGGCGCGGGG  GTCAGAGGGC  GCCGCCACGC  540
cDNA->     ----------  ----------  ----------  ----------  ----------  ---------- gDNA->     TCGCCGAGAC  CGCGTGTTAG  GCTGAGCTAG  GCTTTCATTC  TCGCAGGATC  TACATCAATT  600
cDNA->     ----------  ----------  ----------  ----------  -------ATC  TACATCAATT
Protein                                                                I  Y  I  N --EXON 3--  --EXON 3--  --EXON 3--  --EXON 3--  --EXON 3--  --EXON 3--
gDNA->     ATTACGACAT  GAGCGCGGCC  AACGTGGGCT  GGAACGGCTC  CACCTTCGCT  TGAGTGCCGG  660
cDNA->     ATTACGACAT  GAGCGCGGCC  AACGTGGGCT  GGAACGGCTC  CACCTTCGCT  TGAGTGCCGG
Protein     Y  Y  D  M    S  A  A   N  V  G    W  N  G  S    T  F  A
                                                              Translation STOP --EXON 3--  --EXON 3--  --EXON 3--  --EXON 3--  --EXON 3--  --EXON 3--
gDNA->     CCTAACTTAC  CTGCGCCGCC  GTTTCTTGGA  GCCTTGCTGC  ACGCAGCGTT  CTGTTTTCGT  720
cDNA->     CCTAACTTAC  CTGCGCCGCC  GTTTCTTGGA  GCCTTGCTGC  ACGCAGCGTT  CTGTTTTCGT --EXON 3--  --EXON 3--  --EXON 3--  --EXON 3--  --EXON 3--  --EXON 3--
gDNA->     CCACCCCTGG  CGACGCCCAC  CTTCCGATCG  GGAGAAATAA  ATGGTTTAGA  GACCACGGTT  780
cDNA->     CCACCCCTGG  CGACGCCCAC  CTTCCGATCG  GGAGAAATAA  ATGGTTTAGA  GACCAAAAAA
                                                                            polyA
```

Figure 8
Genomic Structure of the CHO-MIF Locus and ZFN cleavage site
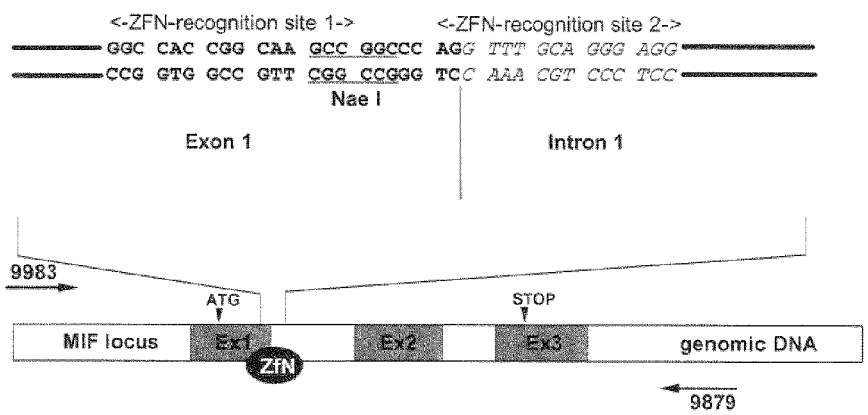
Analysis by PCR and Restriction digest
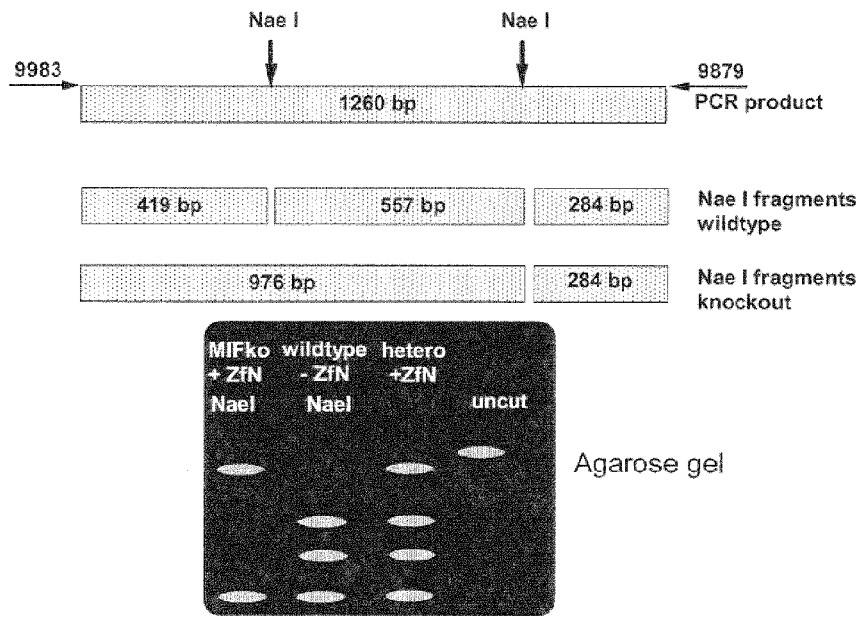

SEQUENCE LISTING

```
<160> NUMBER OF SEQ ID NOS: 35

<210> SEQ ID NO 1
<211> LENGTH: 348
<212> TYPE: DNA
<213> ORGANISM: Cricetulus griseus
<220> FEATURE:
<221> NAME/KEY: CDS
<222> LOCATION: (1)..(348)

<400> SEQUENCE: 1
```

```
atg ccg atg ttc acc gtg aac acc aac gtt ccc cgc gcc tcc gtg cca    48
Met Pro Met Phe Thr Val Asn Thr Asn Val Pro Arg Ala Ser Val Pro
1               5                   10                  15 gag ggg ctt ctc tcc gag ctc acc cag cag ctg gcg cag gcc acc ggc    96
Glu Gly Leu Leu Ser Glu Leu Thr Gln Gln Leu Ala Gln Ala Thr Gly
            20                  25                  30 aag ccg gcc cag tac atc gca gtg cac gtg gtc ccg gac cag ctc atg   144
Lys Pro Ala Gln Tyr Ile Ala Val His Val Val Pro Asp Gln Leu Met
        35                  40                  45 act ttt agc ggc tct agc gac ccc tgc gcc ctg tgc agc ctg cat agt   192
Thr Phe Ser Gly Ser Ser Asp Pro Cys Ala Leu Cys Ser Leu His Ser
    50                  55                  60 atc ggc aag atc ggc ggc gcg cag aac cgc acc tac agc aag ctg ctg   240
Ile Gly Lys Ile Gly Gly Ala Gln Asn Arg Thr Tyr Ser Lys Leu Leu
65                  70                  75                  80 tgc ggc ctg ctg gct gat cgc ctg cac atc agc ccg gac cgg atc tac   288
Cys Gly Leu Leu Ala Asp Arg Leu His Ile Ser Pro Asp Arg Ile Tyr
                85                  90                  95 atc aat tat tac gac atg agc gcg gcc aac gtg ggc tgg aac ggc tcc   336
Ile Asn Tyr Tyr Asp Met Ser Ala Ala Asn Val Gly Trp Asn Gly Ser
            100                 105                 110 acc ttc gct tga                                                   348
Thr Phe Ala
    115

<210> SEQ ID NO 2
<211> LENGTH: 115
<212> TYPE: PRT
<213> ORGANISM: Cricetulus griseus

<400> SEQUENCE: 2

Met Pro Met Phe Thr Val Asn Thr Asn Val Pro Arg Ala Ser Val Pro
1               5                   10                  15

Glu Gly Leu Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Ser Ser Asp Pro Cys Ala Leu Cys Ser Leu His Ser
    50                  55                  60

Ile Gly Lys Ile Gly Gly Ala Gln Asn Arg Thr Tyr Ser Lys Leu Leu
65                  70                  75                  80

Cys Gly Leu Leu Ala Asp Arg Leu His Ile Ser Pro Asp Arg Ile Tyr
                85                  90                  95

Ile Asn Tyr Tyr Asp Met Ser Ala Ala Asn Val Gly Trp Asn Gly Ser
            100                 105                 110

Thr Phe Ala
    115

<210> SEQ ID NO 3
<211> LENGTH: 23
<212> TYPE: DNA
<213> ORGANISM: Artificial
<220> FEATURE:
<223> OTHER INFORMATION: pPCR.MIFspec(1)-8951

<400> SEQUENCE: 3
atgttcrtsg traacaccaa ygt                                          23

<210> SEQ ID NO 4
<211> LENGTH: 21
```

```
<212> TYPE: DNA
<213> ORGANISM: Artificial
<220> FEATURE:
<223> OTHER INFORMATION: pPCR.MIF(4)-8954

<400> SEQUENCE: 4
gcgaaggtgg aryygttcca g                                              21

<210> SEQ ID NO 5
<211> LENGTH: 23
<212> TYPE: DNA
<213> ORGANISM: Artificial
<220> FEATURE:
<223> OTHER INFORMATION: pPCR.choMIF(1) - 9063

<400> SEQUENCE: 5 tgactttag cggctctagc gac                                             23

<210> SEQ ID NO 6
<211> LENGTH: 20
<212> TYPE: DNA
<213> ORGANISM: Artificial
<220> FEATURE:
<223> OTHER INFORMATION: pPCR.choMIF(2) - 9064

<400> SEQUENCE: 6
gatgtgcagg cgatcagcca                                                20

<210> SEQ ID NO 7
<211> LENGTH: 22
<212> TYPE: DNA
<213> ORGANISM: Artificial
<220> FEATURE:
<223> OTHER INFORMATION: pPCR.choMIF - 9196

<400> SEQUENCE: 7
atttctcccg atcggaaggt gg                                             22

<210> SEQ ID NO 8
<211> LENGTH: 19
<212> TYPE: DNA
<213> ORGANISM: Artificial
<220> FEATURE:
<223> OTHER INFORMATION: pPCR.choMIF - 9216

<400> SEQUENCE: 8
ggtgagctcg gagagaagc                                                 19

<210> SEQ ID NO 9
<211> LENGTH: 19
<212> TYPE: DNA
<213> ORGANISM: Artificial
<220> FEATURE:
<223> OTHER INFORMATION: pPCR.choMIF - 9242

<400> SEQUENCE: 9
cggcccagta catcgcagt                                                 19

<210> SEQ ID NO 10
<211> LENGTH: 20
<212> TYPE: DNA
<213> ORGANISM: Artificial
<220> FEATURE:
<223> OTHER INFORMATION: pPCR.choMIF - 9244

<400> SEQUENCE: 10
```

-continued

```
gctgcacgca gcgttctgtt                                              20

<210> SEQ ID NO 11
<211> LENGTH: 24
<212> TYPE: DNA
<213> ORGANISM: Artificial
<220> FEATURE:
<223> OTHER INFORMATION: pPCR.choMIFg - 9983

<400> SEQUENCE: 11
cgttaatctg cagcgtctac ctga                                         24

<210> SEQ ID NO 12
<211> LENGTH: 24
<212> TYPE: DNA
<213> ORGANISM: Artificial
<220> FEATURE:
<223> OTHER INFORMATION: pPCR.choMIFg - 9879

<400> SEQUENCE: 12
gtaaggccac tataggaaag cctg                                         24

<210> SEQ ID NO 13
<211> LENGTH: 19
<212> TYPE: DNA
<213> ORGANISM: Artificial
<220> FEATURE:
<223> OTHER INFORMATION: pPCR.choMIF - 9199

<400> SEQUENCE: 13
gcttctctcc gagctcacc                                               19

<210> SEQ ID NO 14
<211> LENGTH: 840
<212> TYPE: DNA
<213> ORGANISM: Cricetulus griseus

<400> SEQUENCE: 14
ttgggccaca tcccgcgtcg cactgtcctc tactccccgc ttgcagtccc ctccgccacc    60
atgccgatgt tcaccgtgaa caccaacgtt cccgcgcct ccgtgccaga ggggcttctc   120
tccgagctca cccagcagct ggcgcaggcc accggcaagc cggcccaggt ttgcagggag   180
ggtacaggaa gagagagagt gggggagggag ggcccgtgcg cccggccgcc gggcagagga   240
agaatgggga tgggaaccgc ggcgggcggc tggagggctg gaggctggag ctccccggag   300
ccctgtggcc ccgtggtctt tcaggcgggc taaccgcgcg tccacccctc ccccgcagta   360
catcgcagtg cacgtggtcc cggaccagct catgactttt agcggctcta gcgacccctg   420
cgccctgtgc agcctgcata gtatcggcaa gatcggcggc gcgcagaacc gcacctacag   480
caagctgctg tgcggcctgc tggctgatcg cctgcacatc agcccggacc ggtgcgtggg   540
ggtggggtgg ggtgagggc gctgggaggt gggcgcgggg gtcagagggc gccgccacgc   600
tcgccgagac cgcgtgttag gctgagctag gctttcattc tcgcaggatc tacatcaatt   660
attacgacat gagcgcggcc aacgtgggct ggaacggctc caccttcgct tgagtgccgg   720
cctaacttac ctgcgccgcc gtttcttgga gccttgctgc acgcagcgtt ctgttttcgt   780
ccacccctgg cgacgcccac cttccgatcg ggagaaataa atggtttaga gaccacggtt   840

<210> SEQ ID NO 15
<211> LENGTH: 108
<212> TYPE: DNA
<213> ORGANISM: Cricetulus griseus
```

<400> SEQUENCE: 15

```
atgccgatgt tcaccgtgaa caccaacgtt ccccgcgcct ccgtgccaga ggggcttctc    60
tccgagctca cccagcagct ggcgcaggcc accggcaagc cggcccag               108
```

<210> SEQ ID NO 16
<211> LENGTH: 174
<212> TYPE: DNA
<213> ORGANISM: Cricetulus griseus

<400> SEQUENCE: 16

```
tacatcgcag tgcacgtggt cccggaccag ctcatgactt ttagcggctc tagcgacccc    60
tgcgccctgt gcagcctgca tagtatcggc aagatcggcg gcgcgcagaa ccgcacctac   120
agcaagctgc tgtgcggcct gctggctgat cgcctgcaca tcagcccgga ccgg         174
```

<210> SEQ ID NO 17
<211> LENGTH: 193
<212> TYPE: DNA
<213> ORGANISM: Cricetulus griseus

<400> SEQUENCE: 17

```
atctacatca attattacga catgagcgcg gccaacgtgg gctggaacgg ctccaccttc    60
gcttgagtgc cggcctaact tacctgcgcc gccgtttctt ggagccttgc tgcacgcagc   120
gttctgtttt cgtccacccc tggcgacgcc caccttccga tcgggagaaa taaatggttt   180
agagaccaaa aaa                                                     193
```

<210> SEQ ID NO 18
<211> LENGTH: 36
<212> TYPE: PRT
<213> ORGANISM: Cricetulus griseus

<400> SEQUENCE: 18

```
Met Pro Met Phe Thr Val Asn Thr Asn Val Pro Arg Ala Ser Val Pro
1               5                  10                  15

Glu Gly Leu Leu Ser Glu Leu Thr Gln Gln Leu Ala Gln Ala Thr Gly
            20                  25                  30

Lys Pro Ala Gln
        35
```

<210> SEQ ID NO 19
<211> LENGTH: 58
<212> TYPE: PRT
<213> ORGANISM: Cricetulus griseus

<400> SEQUENCE: 19

```
Tyr Ile Ala Val His Val Val Pro Asp Gln Leu Met Thr Phe Ser Gly
1               5                  10                  15

Ser Ser Asp Pro Cys Ala Leu Cys Ser Leu His Ser Ile Gly Lys Ile
            20                  25                  30

Gly Gly Ala Gln Asn Arg Thr Tyr Ser Lys Leu Leu Cys Gly Leu Leu
        35                  40                  45

Ala Asp Arg Leu His Ile Ser Pro Asp Arg
    50                  55
```

<210> SEQ ID NO 20
<211> LENGTH: 21
<212> TYPE: PRT
<213> ORGANISM: Cricetulus griseus

```
<400> SEQUENCE: 20

Ile Tyr Ile Asn Tyr Tyr Asp Met Ser Ala Ala Asn Val Gly Trp Asn
1               5                   10                  15

Gly Ser Thr Phe Ala
            20

<210> SEQ ID NO 21
<211> LENGTH: 35
<212> TYPE: DNA
<213> ORGANISM: Cricetulus griseus
<220> FEATURE:
<221> NAME/KEY: exon
<222> LOCATION: (2)..(22)
<223> OTHER INFORMATION: exon 1, partial
<220> FEATURE:
<221> NAME/KEY: misc_binding
<222> LOCATION: (13)..(18)
<223> OTHER INFORMATION: Nae I restriction site
<220> FEATURE:
<221> NAME/KEY: misc_binding
<222> LOCATION: (16)..(20)
<223> OTHER INFORMATION: ZFN cleavage site
<220> FEATURE:
<221> NAME/KEY: Intron
<222> LOCATION: (23)..(35)
<223> OTHER INFORMATION: intron 1, partial

<400> SEQUENCE: 21 g gcc acc ggc aag ccg gcc cag gtttgcaggg agg                              35
  Ala Thr Gly Lys Pro Ala Gln
  1               5

<210> SEQ ID NO 22
<211> LENGTH: 214
<212> TYPE: PRT
<213> ORGANISM: Artificial Sequence
<220> FEATURE:
<223> OTHER INFORMATION: Light chain of RAB9

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 214
<212> TYPE: PRT
<213> ORGANISM: Artificial Sequence
<220> FEATURE:
<223> OTHER INFORMATION: Light chain of RAB4

<400> SEQUENCE: 23

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 214
<212> TYPE: PRT
<213> ORGANISM: Artificial Sequence
<220> FEATURE:
<223> OTHER INFORMATION: Light chain of RAB0

<400> SEQUENCE: 24

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
```

|    |    |    |    |    |    |    |    |    |    |    |    |
|----|----|----|----|----|----|----|----|----|----|----|----|
|    |    | 35 |    |    |    | 40 |    |    |    | 45 |    |

Ile Tyr Gly Thr Ser Ser Arg Ala Thr Gly Ile Pro Asp Arg Phe Ser
    50                    55                60

Gly Ser Ala Ser Gly Thr Asp Phe Thr Leu Thr Ile Ser Arg Leu Gln
65                  70                    75                    80

Pro Glu Asp Phe Ala Val Tyr Tyr Cys Gln Gln Tyr Gly Arg Ser Leu
                85                  90                95

Thr Phe Gly Gly Gly Thr Lys Val Glu Ile Lys Arg Thr Val Ala Ala
            100              105              110

Pro Ser Val Phe Ile Phe Pro Pro Ser Asp Glu Gln Leu Lys Ser Gly
        115                120              125

Thr Ala Ser Val Val Cys Leu Leu Asn Asn Phe Tyr Pro Arg Glu Ala
        130                135              140

Lys Val Gln Trp Lys Val Asp Asn Ala Leu Gln Ser Gly Asn Ser Gln
145                150                155            160

Glu Ser Val Thr Glu Gln Asp Ser Lys Asp Ser Thr Tyr Ser Leu Ser
        165                170              175

Ser Thr Leu Thr Leu Ser Lys Ala Asp Tyr Glu Lys His Lys Val Tyr
        180                185              190

Ala Cys Glu Val Thr His Gln Gly Leu Ser Ser Pro Val Thr Lys Ser
        195                200              205

Phe Asn Arg Gly Glu Cys
    210

<210> SEQ ID NO 25
<211> LENGTH: 214
<212> TYPE: PRT
<213> ORGANISM: Artificial Sequence
<220> FEATURE:
<223> OTHER INFORMATION: Light chain of RAB2

<400> SEQUENCE: 25

Asp Ile Gln Met Thr Gln Ser Pro Val Thr Leu Ser Leu Ser Pro Gly
1                 5                    10                15

Glu Arg Ala Thr Leu Ser Cys Arg Ala Ser Gln Ser Val Arg Ser Ser
          20                25                30

Tyr Leu Ala Trp Tyr Gln Gln Lys Pro Gly Gln Thr Pro Arg Leu Leu
        35                40              45

Ile Tyr Gly Ala Ser Asn Arg Ala Thr Gly Ile Pro Asp Arg Phe Ser
    50                  55                60

Gly Ser Gly Ser Gly Thr Asp Phe Thr Leu Thr Ile Ser Arg Leu Glu
65                  70                    75                    80

Pro Glu Asp Phe Ala Val Tyr Tyr Cys Gln Gln Tyr Gly Asn Ser Leu
                85                  90                95

Thr Phe Gly Gly Gly Thr Lys Val Glu Ile Lys Arg Thr Val Ala Ala
            100              105              110

Pro Ser Val Phe Ile Phe Pro Pro Ser Asp Glu Gln Leu Lys Ser Gly
        115                120              125

Thr Ala Ser Val Val Cys Leu Leu Asn Asn Phe Tyr Pro Arg Glu Ala
        130                135              140

Lys Val Gln Trp Lys Val Asp Asn Ala Leu Gln Ser Gly Asn Ser Gln
145                150                155            160

Glu Ser Val Thr Glu Gln Asp Ser Lys Asp Ser Thr Tyr Ser Leu Ser
        165                170              175

Ser Thr Leu Thr Leu Ser Lys Ala Asp Tyr Glu Lys His Lys Val Tyr

```
              180                 185                 190
Ala Cys Glu Val Thr His Gln Gly Leu Ser Ser Pro Val Thr Lys Ser
            195                 200                 205

Phe Asn Arg Gly Glu Cys
        210

<210> SEQ ID NO 26
<211> LENGTH: 445
<212> TYPE: PRT
<213> ORGANISM: Artificial Sequence
<220> FEATURE:
<223> OTHER INFORMATION: Heavy chain of RAB9

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
```

```
                    325                 330                 335
Ala Lys Gly Gln Pro Arg Glu Pro Gln Val Tyr Thr Leu Pro Pro Ser
                340                 345                 350
Gln Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 27
<211> LENGTH: 454
<212> TYPE: PRT
<213> ORGANISM: Artificial Sequence
<220> FEATURE:
<223> OTHER INFORMATION: Heavy chain of RAB4

<400> SEQUENCE: 27

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ile Tyr
            20                  25                  30
Ala Met Asp Trp Val Arg Gln Ala Pro Gly Lys Gly Leu Glu Trp Val
        35                  40                  45
Ser Gly Ile Val Pro Ser Gly Gly Phe Thr Lys Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Asn Val Ile Ala Val Ala Gly Thr Gly Tyr Tyr Tyr Tyr
            100                 105                 110
Gly Met Asp Val Trp Gly Gln Gly Thr Thr Val Thr Val Ser Ser Ala
        115                 120                 125
Ser Thr Lys Gly Pro Ser Val Phe Pro Leu Ala Pro Cys Ser Arg Ser
    130                 135                 140
Thr Ser Glu Ser Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Ser Leu Gly Thr Lys Thr Tyr
        195                 200                 205
Thr Cys Asn Val Asp His Lys Pro Ser Asn Thr Lys Val Asp Lys Arg
    210                 215                 220
Val Glu Ser Lys Tyr Gly Pro Pro Cys Pro Pro Cys Pro Ala Pro Glu
225                 230                 235                 240
Phe Leu Gly Gly Pro Ser Val Phe Leu Phe Pro Pro Lys Pro Lys Asp
```

```
                245                 250                 255
Thr Leu Met Ile Ser Arg Thr Pro Glu Val Thr Cys Val Val Asp
        260                 265                 270

Val Ser Gln Glu Asp Pro Glu Val Gln Phe Asn Trp Tyr Val Asp Gly
    275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Leu Gly Lys
    450

<210> SEQ ID NO 28
<211> LENGTH: 454
<212> TYPE: PRT
<213> ORGANISM: Artificial Sequence
<220> FEATURE:
<223> OTHER INFORMATION: Heavy chain of RAB0

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
```

```
                145                 150                 155                 160
        Pro Glu Pro Val Thr Val Ser Trp Asn Ser Gly Ala Leu Thr Ser Gly
                        165                 170                 175
        Val His Thr Phe Pro Ala Val Leu Gln Ser Ser Gly Leu Tyr Ser Leu
                        180                 185                 190
        Ser Ser Val Val Thr Val Pro Ser Ser Ser Leu Gly Thr Lys Thr Tyr
                        195                 200                 205
        Thr Cys Asn Val Asp His Lys Pro Ser Asn Thr Lys Val Asp Lys Arg
                210                 215                 220
        Val Glu Ser Lys Tyr Gly Pro Pro Cys Pro Pro Cys Pro Ala Pro Glu
        225                 230                 235                 240
        Phe Leu Gly Gly Pro Ser Val Phe Leu Phe Pro Pro Lys Pro Lys Asp
                        245                 250                 255
        Thr Leu Met Ile Ser Arg Thr Pro Glu Val Thr Cys Val Val Val Asp
                        260                 265                 270
        Val Ser Gln Glu Asp Pro Glu Val Gln Phe Asn Trp Tyr Val Asp Gly
                        275                 280                 285
        Val Glu Val His Asn Ala Lys Thr Lys Pro Arg Glu Glu Gln Phe Asn
                290                 295                 300
        Ser Thr Tyr Arg Val Val Ser Val Leu Thr Val Leu His Gln Asp Trp
        305                 310                 315                 320
        Leu Asn Gly Lys Glu Tyr Lys Cys Lys Val Ser Asn Lys Gly Leu Pro
                        325                 330                 335
        Ser Ser Ile Glu Lys Thr Ile Ser Lys Ala Lys Gly Gln Pro Arg Glu
                        340                 345                 350
        Pro Gln Val Tyr Thr Leu Pro Pro Ser Gln Glu Glu Met Thr Lys Asn
                        355                 360                 365
        Gln Val Ser Leu Thr Cys Leu Val Lys Gly Phe Tyr Pro Ser Asp Ile
                370                 375                 380
        Ala Val Glu Trp Glu Ser Asn Gly Gln Pro Glu Asn Asn Tyr Lys Thr
        385                 390                 395                 400
        Thr Pro Pro Val Leu Asp Ser Asp Gly Ser Phe Phe Leu Tyr Ser Arg
                        405                 410                 415
        Leu Thr Val Asp Lys Ser Arg Trp Gln Glu Gly Asn Val Phe Ser Cys
                        420                 425                 430
        Ser Val Met His Glu Ala Leu His Asn His Tyr Thr Gln Lys Ser Leu
                        435                 440                 445
        Ser Leu Ser Leu Gly Lys
                450

<210> SEQ ID NO 29
<211> LENGTH: 454
<212> TYPE: PRT
<213> ORGANISM: Artificial Sequence
<220> FEATURE:
<223> OTHER INFORMATION: Heavy chain of RAB2

<400> SEQUENCE: 29

Glu Val Gln Leu Leu Glu Ser Gly Gly Gly Leu Val Gln Pro Gly Gly
        1               5                   10                  15
        Ser Leu Arg Leu Ser Cys Ala Ala Ser Gly Phe Thr Phe Ser Ile Tyr
                        20                  25                  30
        Ala Met Asp Trp Val Arg Gln Ala Pro Gly Lys Gly Leu Glu Trp Val
                        35                  40                  45
        Ser Gly Ile Val Pro Ser Gly Gly Phe Thr Lys Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Val Ile Ala Val Ala Gly Thr Gly Tyr Tyr Tyr Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Cys Ser Arg Ser
                130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Lys Thr Tyr
                195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser Gln Glu Asp Pro Glu Val Gln Phe Asn Trp Tyr Val Asp Gly
                275                 280                 285

Val Glu Val His Asn Ala Lys Thr Lys Pro Arg Glu Glu Gln Phe Asn
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Leu Gly Lys
450

<210> SEQ ID NO 30
```

```
<211> LENGTH: 457
<212> TYPE: PRT
<213> ORGANISM: Artificial Sequence
<220> FEATURE:
<223> OTHER INFORMATION: RAM0hc

<400> SEQUENCE: 30
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Trp | Tyr |
| | | | 20 | | | | | 25 | | | | | 30 | | |
| Ala | Met | Asp | Trp | Val | Arg | Gln | Ala | Pro | Gly | Lys | Gly | Leu | Glu | Trp | Val |
| | | | 35 | | | | | 40 | | | | | 45 | | |
| Ser | Gly | Ile | Tyr | Pro | Ser | Gly | Gly | Arg | Thr | Lys | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Val | Asn | Val | Ile | Ala | Val | Ala | Gly | Thr | Gly | Tyr | Tyr | Tyr | Tyr |
| | | | | 100 | | | | | 105 | | | | | 110 | |
| Gly | Met | Asp | Val | Trp | Gly | Gln | Gly | Thr | Thr | Val | Thr | Val | Ser | Ser | Ala |
| | | | 115 | | | | | 120 | | | | | 125 | | |
| Ser | Thr | Lys | Gly | Pro | Ser | Val | Phe | Pro | Leu | Ala | Pro | Ser | Ser | Lys | Ser |
| 130 | | | | | 135 | | | | | 140 | | | | | |
| Thr | Ser | Gly | Gly | Thr | Ala | Ala | Leu | Gly | Cys | Leu | Val | Lys | Asp | Tyr | Phe |
| 145 | | | | | 150 | | | | | 155 | | | | | 160 |
| Pro | Glu | Pro | Val | Thr | Val | Ser | Trp | Asn | Ser | Gly | Ala | Leu | Thr | Ser | Gly |
| | | | | 165 | | | | | 170 | | | | | 175 | |
| Val | His | Thr | Phe | Pro | Ala | Val | Leu | Gln | Ser | Ser | Gly | Leu | Tyr | Ser | Leu |
| | | | 180 | | | | | 185 | | | | | 190 | | |
| Ser | Ser | Val | Val | Thr | Val | Pro | Ser | Ser | Ser | Leu | Gly | Thr | Gln | Thr | Tyr |
| | | | 195 | | | | | 200 | | | | | 205 | | |
| Ile | Cys | Asn | Val | Asn | His | Lys | Pro | Ser | Asn | Thr | Lys | Val | Asp | Lys | Arg |
| | 210 | | | | | 215 | | | | | 220 | | | | |
| Val | Glu | Pro | Lys | Ser | Cys | Asp | Lys | Thr | His | Thr | Cys | Pro | Pro | Cys | Pro |
| 225 | | | | | 230 | | | | | 235 | | | | | 240 |
| Ala | Pro | Glu | Leu | Leu | Gly | Gly | Pro | Ser | Val | Phe | Leu | Phe | Pro | Pro | Lys |
| | | | | 245 | | | | | 250 | | | | | 255 | |
| Pro | Lys | Asp | Thr | Leu | Met | Ile | Ser | Arg | Thr | Pro | Glu | Val | Thr | Cys | Val |
| | | | 260 | | | | | 265 | | | | | 270 | | |
| Val | Val | Asp | Val | Ser | His | Glu | Asp | Pro | Glu | Val | Lys | Phe | Asn | Trp | Tyr |
| | | | 275 | | | | | 280 | | | | | 285 | | |
| Val | Asp | Gly | Val | Glu | Val | His | Asn | Ala | Lys | Thr | Lys | Pro | Arg | Glu | Glu |
| | 290 | | | | | 295 | | | | | 300 | | | | |
| Gln | Tyr | Asn | Ser | Thr | Tyr | Arg | Val | Val | Ser | Val | Leu | Thr | Val | Leu | His |
| 305 | | | | | 310 | | | | | 315 | | | | | 320 |
| Gln | Asp | Trp | Leu | Asn | Gly | Lys | Glu | Tyr | Lys | Cys | Lys | Val | Ser | Asn | Lys |
| | | | | 325 | | | | | 330 | | | | | 335 | |
| Ala | Leu | Pro | Ala | Pro | Ile | Glu | Lys | Thr | Ile | Ser | Lys | Ala | Lys | Gly | Gln |
| | | | 340 | | | | | 345 | | | | | 350 | | |
| Pro | Arg | Glu | Pro | Gln | Val | Tyr | Thr | Leu | Pro | Pro | Ser | Arg | Glu | Glu | Met |
| | | | 355 | | | | | 360 | | | | | 365 | | |
| Thr | Lys | Asn | Gln | Val | Ser | Leu | Thr | Cys | Leu | Val | Lys | Gly | Phe | Tyr | Pro |
| | 370 | | | | | 375 | | | | | 380 | | | | |

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 31
<211> LENGTH: 214
<212> TYPE: PRT
<213> ORGANISM: Artificial Sequence
<220> FEATURE:
<223> OTHER INFORMATION: RAM01c

<400> SEQUENCE: 31

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 448
<212> TYPE: PRT
<213> ORGANISM: Artificial Sequence
<220> FEATURE:
<223> OTHER INFORMATION: RAM9hc

<400> SEQUENCE: 32

Glu Val Gln Leu Leu Glu Ser Gly Gly Gly Leu Val Gln Pro Gly Gly

```
1               5                   10                  15
Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
            35                  40                  45

Ser Ser Ile Gly Ser Ser Gly Gly Thr Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445
```

<210> SEQ ID NO 33
<211> LENGTH: 214
<212> TYPE: PRT
<213> ORGANISM: Artificial Sequence
<220> FEATURE:
<223> OTHER INFORMATION: RAM91c

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 34
<211> LENGTH: 457
<212> TYPE: PRT
<213> ORGANISM: Artificial Sequence
<220> FEATURE:
<223> OTHER INFORMATION: RAM4hc

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
50                  55                  60

Lys Gly Arg Phe Thr Ile Ser Arg Asp Asn Ser Lys Asn Thr Leu Tyr
```

```
                65                  70                  75                  80
        Leu Gln Met Asn Ser Leu Arg Ala Glu Asp Thr Ala Val Tyr Tyr Cys
                            85                  90                  95

Ala Arg Val Asn Val Ile Ala Val Ala Gly Thr Gly Tyr Tyr Tyr Tyr
                        100                 105                 110

Gly Met Asp Val Trp Gly Gln Gly Thr Thr Val Thr Val Ser Ser Ala
                    115                 120                 125

Ser Thr Lys Gly Pro Ser Val Phe Pro Leu Ala Pro Ser Ser Lys Ser
                130                 135                 140

Thr Ser Gly Gly Thr Ala Ala Leu Gly Cys Leu Val Lys Asp Tyr Phe
        145                 150                 155                 160

Pro Glu Pro Val Thr Val Ser Trp Asn Ser Gly Ala Leu Thr Ser Gly
                            165                 170                 175

Val His Thr Phe Pro Ala Val Leu Gln Ser Ser Gly Leu Tyr Ser Leu
                        180                 185                 190

Ser Ser Val Val Thr Val Pro Ser Ser Ser Leu Gly Thr Gln Thr Tyr
                    195                 200                 205

Ile Cys Asn Val Asn His Lys Pro Ser Asn Thr Lys Val Asp Lys Arg
                210                 215                 220

Val Glu Pro Lys Ser Cys Asp Lys Thr His Thr Cys Pro Pro Cys Pro
        225                 230                 235                 240

Ala Pro Glu Leu Leu Gly Gly Pro Ser Val Phe Leu Phe Pro Pro Lys
                            245                 250                 255

Pro Lys Asp Thr Leu Met Ile Ser Arg Thr Pro Glu Val Thr Cys Val
                        260                 265                 270

Val Val Asp Val Ser His Glu Asp Pro Glu Val Lys Phe Asn Trp Tyr
                    275                 280                 285

Val Asp Gly Val Glu Val His Asn Ala Lys Thr Lys Pro Arg Glu Glu
                290                 295                 300

Gln Tyr Asn Ser Thr Tyr Arg Val Val Ser Val Leu Thr Val Leu His
        305                 310                 315                 320

Gln Asp Trp Leu Asn Gly Lys Glu Tyr Lys Cys Lys Val Ser Asn Lys
                            325                 330                 335

Ala Leu Pro Ala Pro Ile Glu Lys Thr Ile Ser Lys Ala Lys Gly Gln
                        340                 345                 350

Pro Arg Glu Pro Gln Val Tyr Thr Leu Pro Pro Ser Arg Glu Glu Met
                    355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
        385                 390                 395                 400

Tyr Lys Thr Thr Pro Pro Val Leu Asp Ser Asp Gly Ser Phe Phe Leu
                            405                 410                 415

Tyr Ser Lys Leu Thr Val Asp Lys Ser Arg Trp Gln Gln Gly Asn Val
                        420                 425                 430

Phe Ser Cys Ser Val Met His Glu Ala Leu His Asn His Tyr Thr Gln
                    435                 440                 445

Lys Ser Leu Ser Leu Ser Pro Gly Lys
                450                 455

<210> SEQ ID NO 35
<211> LENGTH: 214
<212> TYPE: PRT
<213> ORGANISM: Artificial Sequence
```

<220> FEATURE:
<223> OTHER INFORMATION: RAM41c

<400> SEQUENCE: 35

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

CHARACTERIZATION OF CHO-MIF GENE AND PROTEIN, AND USE THEREOF

CROSS-REFERENCES TO RELATED APPLICATIONS

The present application is a U.S. National Phase Application of International Patent Application No. PCT/EP2012/069602, filed Oct. 4, 2012, which claims the benefit of U.S. Provisional Patent Application 61/545,047 filed Oct. 7, 2011, which are expressly incorporated herein by reference in their entireties for all purposes.

The present invention is based on the identification and characterization of the CHO-MIF gene. This allowed the provision of CHO-MIF knock-out cells and formed the basis a highly sensitive detection method of specific OHO-MIF complexes, particularly in the production of anti-MIF antibodies. The present invention is further concerned with the provision of an advantageous polyclonal rabbit antiserum which can be used for a CHO-MIF detection method. Furthermore, a method is shown, to avoid any contaminations of anti-MIF antibodies with CHO-MIF by knocking out the endogenous gene in CHO cells.

BACKGROUND

Macrophage migration inhibitory factor (MIF) is a cytokine initially isolated based upon its ability to inhibit the in vitro random migration of peritoneal exudate cells from tuberculin hypersensitive guinea pigs (containing macrophages) (Bloom et al. Science 1966, 153, 80-2; David et al. PNAS 1966, 56, 72-7). Today, MIF is known as a critical upstream regulator of the innate and acquired immune response that exerts a pleiotropic spectrum of activities.

The human MIF cDNA was cloned in 1989 (Weiser et al., PNAS 1989, 86, 7522-6), and its genomic localization was mapped to chromosome 22. The product of the human MIF gene is a protein with 114 amino acids (after cleavage of the N-terminal methionine) and an apparent molecular mass of about 12.5 kDa. MIF has no significant sequence homology to any other protein. The protein crystallizes as a trimer of identical subunits. Each monomer contains two antiparallel alpha-helices that pack against a four-stranded beta-sheet. The monomer has additional two beta-strands that interact with the beta-sheets of adjacent subunits to form the interface between monomers. The three subunits are arranged to form a barrel containing a solvent-accessible channel that runs through the center of the protein along a molecular three-fold axis (Sun et al. PNAS 1996, 93, 5191-5196).

It was reported that MIF secretion from macrophages was induced at very low concentrations of glucocorticoids (Calandra et al. Nature 1995, 377, 68-71). However, MIF also counter-regulates the effects of glucocorticoids and stimulates the secretion of other cytokines such as tumor necrosis factor TNF-α and interleukin IL-1β (Baugh et al., Crit. Care Med 2002, 30, S27-35). MIF was also shown e.g. to exhibit pro-angiogenic, pro-proliferative and anti-apoptotic properties, thereby promoting tumor cell growth (Mitchell, R. A., Cellular Signalling, 2004. 16(1): p. 13-19; Lue, H. et al., Oncogene 2007. 26(35): p. 5046-59). It is also e.g. directly associated with the growth of lymphoma, melanoma, and colon cancer (Nishihira et al. J Interferon Cytokine Res. 2000, 20:751-62).

MIF is a mediator of many pathologic conditions and thus associated with a variety of diseases including inter alia inflammatory bowel disease (IBD), rheumatoid arthritis (RA), acute respiratory distress syndrome (ARDS), asthma, glomerulonephritis, IgA nephropathy, myocardial infarction (MI), sepsis and cancer, though not limited thereto.

Polyclonal and monoclonal anti-MIF antibodies have been developed against recombinant human MIF (Shimizu et al., FEBS Lett. 1996; 381, 199-202; Kawaguchi et al, Leukoc. Biol. 1986, 39, 223-232, and Weiser et al., Cell. Immunol. 1985, 90, 16778).

Anti-MIF antibodies have been suggested for therapeutic use. Calandra et al., (J. Inflamm. 1995. 47, 39-51) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states.

U.S. Pat. No. 6,645,493 discloses monoclonal anti-MIF antibodies derived from hybridoma cells, which neutralize the biological activity of MIF. It could be shown in an animal model that these mouse-derived anti-MIF antibodies had a beneficial effect in the treatment of endotoxin induced shock.

US 200310235584 discloses methods of preparing high affinity antibodies to MIF in animals in which the MIF gene has been homozygously knocked-out.

Glycosylation-inhibiting factor (GIF) is a protein described by Galat et al. (Eur. J. Biochem, 1994, 224, 417-21). MIF and GIF are now recognized to be identical. Watarai et al. (PNAS 2000, 97, 13251-6) described polyclonal antibodies binding to different GIF epitopes to identify the biochemical nature of the posttranslational modification of GIF in Ts cells.

In view of the clear biological significance of MIF/GIF, is therefore necessary and would be highly desirable to provide purified anti-MIF antibodies as diagnostic and therapeutic tools.

Clearly, therefore a need exists for the production of anti-MIF antibodies, whereby these are free from contaminations.

Various methods for the production of anti-MIF antibodies are currently available. One major approach is to use the recombinant production of anti-MIF antibodies whereby a host cell expresses the desired anti-MIF antibody product. Chinese hamster ovary (CHO) cells are a cell line derived from the ovary of the Chinese hamster (*Cricetulus griseus*). They are frequently and broadly used in biological and medical research production of therapeutic proteins, e.g. antibodies.

Today, CHO cells are the most commonly used mammalian hosts for industrial production of recombinant protein therapeutics, including antibodies.

CHO cells have been a cell line of choice because of their rapid growth and high protein production. They have become the mammalian equivalent of *E. coli* in research and biotechnology today, especially when long-term, stable gene expression and high yields of proteins are required.

However, the present inventors, upon investigation of a possible preferable production and purification process of anti-MIF antibodies with the use of CHO cells as host cells discovered that CHO cells themselves produce MIF. This is surprisingly different from the situation e.g. when preparing MIF from hybridoma cells or in the preparation of polyclonal antisera where no such or corresponding contaminations are found. The MIF as produced by CHO cells is a Chinese hamster MIF, due to the fact that CHO cells are derived from ovary cells of a Chinese hamster. This "Chinese hamster-MIF" (in the following and above also designated as "CHO-MIF"), possibly because of the high homology between CHO-MIF and other, e.g. human, MIF also binds to the anti-MIF antibodies to be produced. Thus, endogenous CHO-MIF could possibly contaminate the final CHO-cell based preparations of antibodies directed to non-CHO-MIF (e.g. complexed to the desired anti-MIF antibodies), like e.g. human MIF, or mouse MIF.

Therefore, there exists a need for the provision of a cell line which does not produce possibly contaminating CHO-MIF; a further need exists for a sensitive method to detect minor amounts of CHO-MIF contaminations in preparations of anti-MIF antibodies produced in CHO cells producing the CHO-MIF and a specific method for the production and purification of such anti-MIF antibody preparations which are not contaminated by CHO-MIF. As a prerequisite for both the provision of an essentially CHO-MIF free CHO cell line and for developing a sensitive detection method for potential CHO-MIF contaminations, there exists a need to identify and characterize the CHO-MIF gene as a starting point for solving the problems mentioned above.

There also exists a need for such a CHO-MIF cell line which provides similar growth and production characteristics as the wild type CHO cell line.

DESCRIPTION OF THE INVENTION

The present inventors have succeeded in identifying and characterizing the CHO-MIF gene. On that basis they further succeeded in the provision of tools and methods allowing production and testing of anti-MIF antibody preparations in CHO cells, which preparations are essentially free of contaminating CHO-MIF. These tools and methods further allowed production and testing of all recombinant preparations as produced in CHO cells, which comprise recombinant CHO-MIF-binding protein, whereupon these preparations are essentially free of contaminating CHO-MIF. A recombinant CHO MIF binding protein in that context is a protein which binds to CHO MIF; thus, the protein binds to CHO MIF under immunoassay conditions, whereby a variety of immunoassay formats can be used to determine this binding, as is well known to a person skilled in the art. For example, solid phase ELISA immunoassays are routinely used to determine such binding reactions; see Harlow and Lane (1988), Antibodies, A Laboratory Manual, Col Spring harbour publications, New York, for a description of immunoassay formats and conditions that can be used.

Thus, the present invention is directed to the analysis of the gene locus coding for CHO-MIF. This allows the generation of MIF knockout CHO cells producing recombinant antibodies or other products, preferably antibodies directed towards human MIF, essentially without any CHO-MIF contaminants.

The present invention is further directed to a knock-out cell line wherein the CHO-MIF gene is successfully knocked out.

The present invention is also directed to a highly sensitive method for the detection of ppm levels of CHO-MIF which during production in CHO cells of products, in particular antibodies and even more preferred anti-MIF antibodies or antigen-binding fragments thereof, can remain attached to the desired product in some cases. In a preferred embodiment, this detection method is based on the generation and purification of highly specific anti CHO-MIF antibodies which are affinity-purified polyclonal rabbit antibodies.

Only with a detection method, as described in the present invention, which is able to detect CHO-MIF in very minor amounts, it can be ensured that a final preparation is pure and in particular free of CHO-MIF. Thereby, the present inventors succeeded in providing a recombinant product preparation, produced in CHO cells, comprising a product which would bind to CHO-MIF, in the event that CHO-MIF was present, wherein said preparation is essentially free of CHO-MIF. Preferably, the product as produced in the CHO cells is an antibody, more preferred an anti-MIF antibody, very preferred an anti human MIF antibody.

Preferred embodiments of these anti human MIF antibodies are described below and are designated as RAB4, RAB0, RAB9, RAM4, RAM0, and RAM9 respectively.

The present invention thus provides a recombinant preparation, as defined above, which satisfies quality control requirements, in particular with regard to the essential absence of CHO-MIF contaminations.

The present invention is further directed to the isolation of mRNA coding for CHO-MIF as produced by CHO cells. According to the invention, the cDNA created by reverse transcription of this mRNA is cloned into a prokaryotic expression vector. The CHO-MIF protein expressed thereof in *E. coli* is purified to homogeneity. The recombinant CHO-MIF is used to immunize rabbits in order to generate the inventive polyclonal rabbit antibodies specific to CHO-MIF.

DETAILED DESCRIPTION OF THE INVENTION

Definitions and Techniques

Unless otherwise defined herein, scientific and technical terms used in connection with the present invention shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), which are incorporated herein by reference.

"MIF" or "macrophage migration inhibitory factor" refers to the protein, which is known as a critical mediator in the immune and inflammatory response, especially as a counter-regulator of glucocorticoids. MIF includes mammalian MIF, specifically human MIF (Swiss-Prot primary accession number: P14174), wherein the monomeric form is encoded as a 115 amino acid protein but is produced as a 114 amino acid protein due to cleavage of the initial methionine. "MIF" also includes what was formerly known as "GIF" (glycosylation-inhibiting factor).

Also known are MIF derivatives/fragments, which exhibit functional or immunological properties of MIF, such as e.g. fragments or fusion proteins of MIF.

An "antibody" in this application refers to an intact antibody or an antigen-binding portion that competes with the intact antibody for specific binding. See generally, Fundamental Immunology, Ch. 7 (Paul, W., ed., 2nd ed. Raven Press, N.Y. (1989)) (incorporated by reference). The term antibody includes human antibodies, mammalian antibodies, isolated antibodies and genetically engineered forms such as, but not limited to, chimeric, camelized or humanized antibodies.

The term "antigen-binding portion" of an antibody refers to one or more fragments of an antibody that retain the ability to specifically bind to an antigen (e.g. MIF). Antigen-binding portions may be produced by recombinant DNA techniques or by enzymatic or chemical cleavage of intact antibodies. Antigen-binding portions include Fab, Fab', F(ab')2, Fv, and complementarity determining regions (CDR) and fragments thereof, single-chain antibodies (scFv), chimeric antibodies, antibodies and polypeptides, that contain at least a portion of an antibody that is sufficient to confer specific antigen binding to the polypeptide. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et al. J. Mol. Biol. 196:901-917 (1987), or Chothia et al., Nature 342:878-883 (1989). An antibody or antigen-binding portion thereof can be derivatized or linked to another functional molecule (e.g. another peptide or protein). For example, an antibody or antigen-binding portion thereof can be functionally linked to one or more other molecular entities, such as another antibody (e.g. a bispecific antibody or a diabody), a detectable agent, a cytotoxic agent, a pharmaceutical agent, and/or a linking molecule.

The term "human antibody" refers to any antibody in which the variable and constant domains are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells.

The term "humanized antibody" refers to antibodies comprising human sequences and containing additionally non-human sequences.

The term "camelized antibody" refers to antibodies wherein the antibody structure or sequence has changed to more closely resemble antibodies from camels, also designated camelid antibodies. Methods for the design and production of camelized antibodies are part of the general knowledge of a person skilled in the art.

The term "chimeric antibody" refers to an antibody that comprises regions from two or more different species.

The term "isolated antibody" or "isolated antigen-binding portion thereof" refers to an antibody or an antigen-binding portion thereof that has been identified and selected from an antibody source such as a phage display library or a B-cell repertoire and has then been e.g. recombinantly prepared.

The term "polyclonal antibody" refers to a polyclonal antibody preparation, which may be a purified or partially purified polyclonal antibody fraction or which may be used in form of a crude serum from an animal immunized with the respective antigen, e.g. purified CHO-MIF.

The term "$K_D$" refers to the equilibrium dissociation constant of a Fab portion of a particular antibody with the respective antigen.

The term "epitope" includes any protein determinant capable of specific binding to an immunoglobulin or an antibody fragment. Epitopic determinants usually consist of chemically active surface groupings of molecules such as exposed amino acids, amino sugars, or other carbohydrate side chains and usually have specific three-dimensional structural characteristics, as well as specific charge characteristics.

The term "vector" refers to a nucleic acid molecule capable of transporting another nucleic acid to which it has been linked. In some embodiments, the vector is a plasmid, i.e., a circular double stranded DNA loop into which additional DNA segments may be ligated.

The term "host cell" refers to a cell line, which is capable to produce a recombinant protein after introducing an expression vector. The term "recombinant cell line" refers to a cell line into which a recombinant expression vector has been introduced. It should be understood that "recombinant cell line" does not only mean the particular subject cell line but also the progeny of such a cell line. Because certain modifications may occur in succeeding generations due to either mutation or environmental influences, such progeny may not, in fact, be identical to the parent cell, but is still included within the scope of the term "recombinant cell line" as used herein. The host cell as used according to the present invention is a CHO cell line.

The term "Western Blot" refers to the well-known and established technique of blotting proteins on a carrier membrane whereupon these proteins can subsequently be detected. The transfer to the membrane is carried out by well-known methods, of which diffusion, application of capillary forces or electrophoresis are examples, which however are by no means limiting the present method. In the case of an immunoblot, the detection is carried out by use of monoclonal or polyclonal antibodies. A "semi-quantitative" Western Blot in the context of the present invention means a Western Blot where the signal intensity from a sample (e.g. CHO-MIF which can in some cases appear in complex with an anti-MIF antibody) is compared with the signal intensity from the corresponding standards (e.g. CHO-MIF). The signal can be e.g. a chemiluminescent signal quantified e.g. electronically by digital imaging systems.

BRIEF DESCRIPTION OF THE FIGURES

The present invention is further described in the following figures:

FIG. 1: describes the nucleotide and amino acid sequence of the CHO-MIF coding region (SEQ ID NO: 1). Lane 1 shows the number of the amino acids starting with the ATG as position +1. Lane 2 depicts the names of the amino acids. Lane 3 shows the DNA sequence triplets coding for these amino acids. Lane 4 shows the numbering of the base pairs. The total length of CHO-MIF is 115 amino acids translated from 345 base pairs.

FIG. 2: shows the organization of the CHO-MIF locus. The genomic DNA (lane 2: gDNA, SEQ ID NO: 14) is organized in 3 exons, separated by two introns as explained in lane 1. The cDNA (lane 3, SEQ ID NOs: 15 (exon 1), 16 (exon 2) and 17 (exon 3)) is translated into the CHO-MIF protein sequence shown in lane 4 (SEQ ID NOs: 18 (exon 1), 19 (exon 2) and 20 (exon 3)). The 3'-untranslated region of the cDNA is shown after the translational stop codon TGA to the polyA tail. The translated parts of the gene are framed.

Lane 1: 2 ng CHO-MIF (corresponding to 4 ppm CHO-MIF impurity in 500 µg human anti-MIF antibodies);
lane 2: 1 ng CHO-MIF (corresponding to 2 ppm CHO-MIF impurity in 500 µg human anti-MIF antibodies);
lane 3: 0.5 ng CHO-MIF (corresponding to 1 ppm CHO-MIF impurity in 500 µg human anti-MIF antibodies);
lane 4: 0.25 ng CHO-MIF (corresponding to 0.5 ppm CHO-MIF impurity in 500 µg human anti-MIF antibodies);
lane M: molecular weight protein marker.

Figure 7:
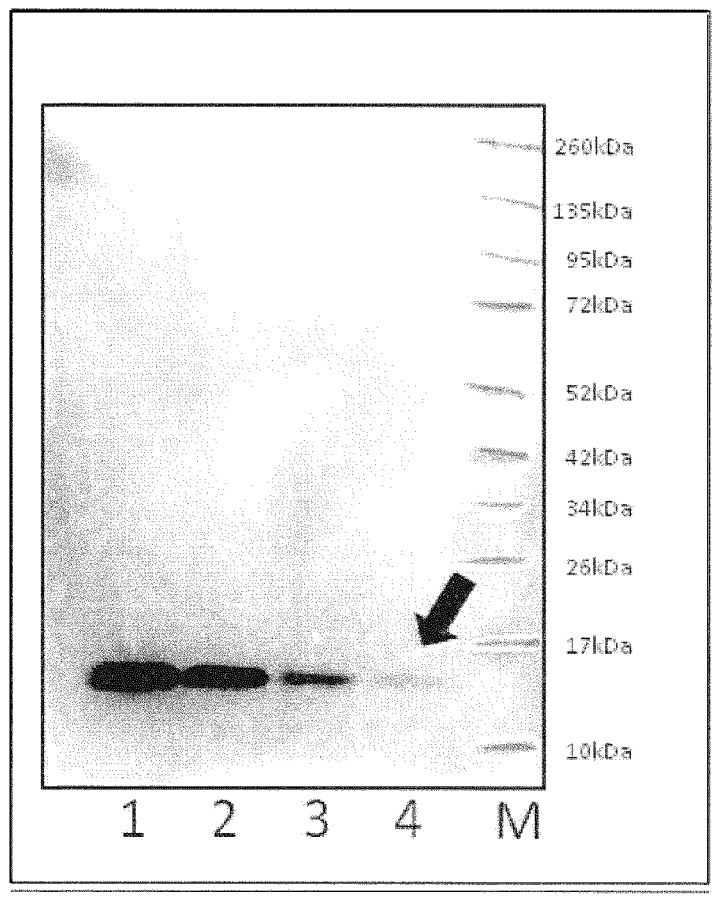
FIG. 7: shows a Western Blot with different amounts of CHO-MIF detected by the affinity purified rabbit anti CHO-MIF antibodies (3.5 µg/mL, HRP conjugate 1:6000, same conditions as described in Example 5). This Western Blot is an example for the sensitivity of the rabbit anti CHO-MIF antibodies. The lowest amount of CHO-MIF detected by the rabbit anti CHO-MIF antibodies was 0.25 ng/lane (corresponding to 0.5 ppm in 500 µg human anti-MIF antibody preparation).
Figure 7A:
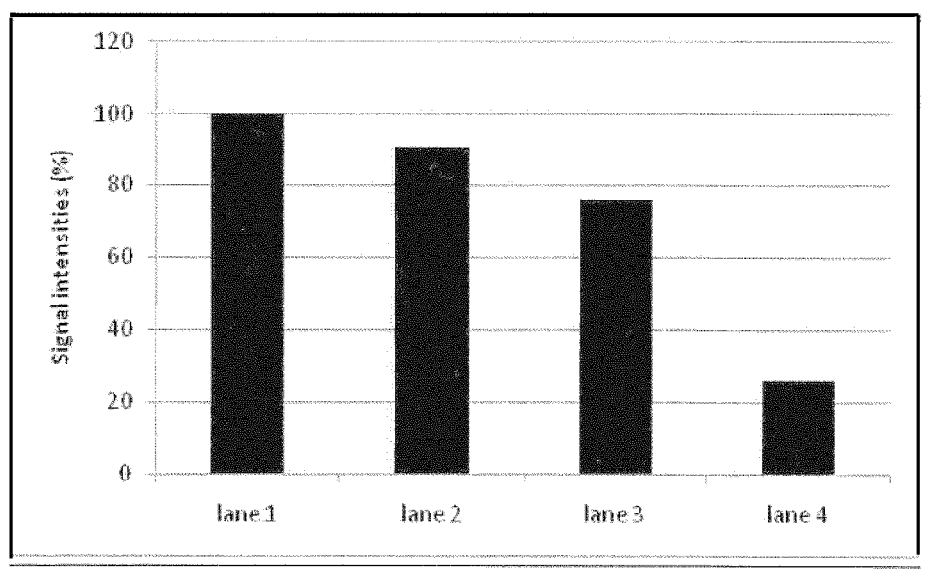

FIG. 7a: is a bar chart of the CHO-MIF protein signals resultant from a Western Blot as shown in FIG. 7. To that end, the CHO-MIF signals were scanned by a LAS4000 (Fujifilm Life Science®) using the Image Reader LAS4000 Scanner Software® and directly quantified by the Image Quant LAS4000® software. The 2 ng CHO-MIF signal from lane 1 was set to 100% and directly compared to the other CHO-MIF signals. 90% of the 100% reference signal was found 1 ng recombinant CHO-MIF as shown in lane/bar 2; 76% of the 100% reference signal was found for the 0.5 ng CHO-MIF protein shown in lane/bar 3; 26% of the 100% reference signal was found for the 0.25 ng CHO-MIF protein shown in lane/bar 4.

FIG. 8: is a cartoon showing the position and recognition site of the Zinc finger nuclease (ZFN) at the boundary of exon1/intron1 of the MIF locus (SEQ ID NO: 21). The lower part illustrates the strategy for the genetic characterization of MIF knockout clones. Exon 1 is shown in bold letters; Intron 1 in italics. The 5 basepair cleavage site GGCCC is in between the 15 bp recognition sites of the two Zinc finger nuclease subunits. The NaeI restriction site GCCGGC is underlined.

Two PCR primers, 9983 (SEQ ID NO: 11) and 9879 (SEQ ID NO: 12) binding in the CHO-MIF locus outside the translated region were designed. Using these 2 primers, a 1260 bp fragment can be amplified by PCR containing 2 NaeI sites in the case of the wildtype fragment. Due to the ZFN treatment, the first NaeI site is expected to be destroyed. In case of a wildtype gene locus the 1260 bp fragment a NaeI digest results in 3 fragments, in case of a knockout only 2 fragments are generated. The expected pattern after separation on a DNA-agarose gel is shown on the cartoon of a gel (lane 1 knockout, lane 2 wildtype) As CHO cells are expected to be diploid, a heterozygous constellation as shown in lane 3 is expected FIG. 9: shows an agarose gel of the genetic analysis of individual CHO cell clones producing antibody RAB0 isolated after treatment with the Zinc finger nuclease. A PCR fragment spanning the gene locus of MIF is digested with NaeI and separated on an agarose gel as described in FIG. 8. Five cell lines are homozygous MIF knockout (lanes 2,3; 4,5; 8,9; 10,11; 12,13). One cell line (lane 6,7) is heterozygous. The original wildtype cell line is shown in lane 14, 15.

Figure 9:
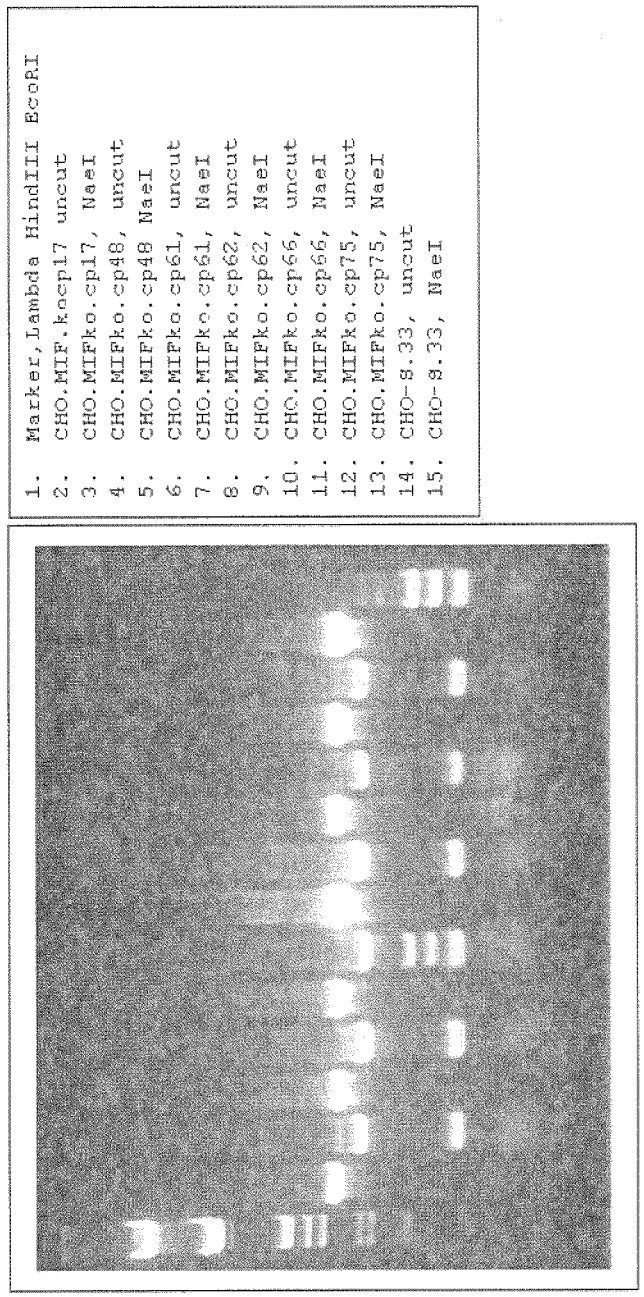
Figure 9A:
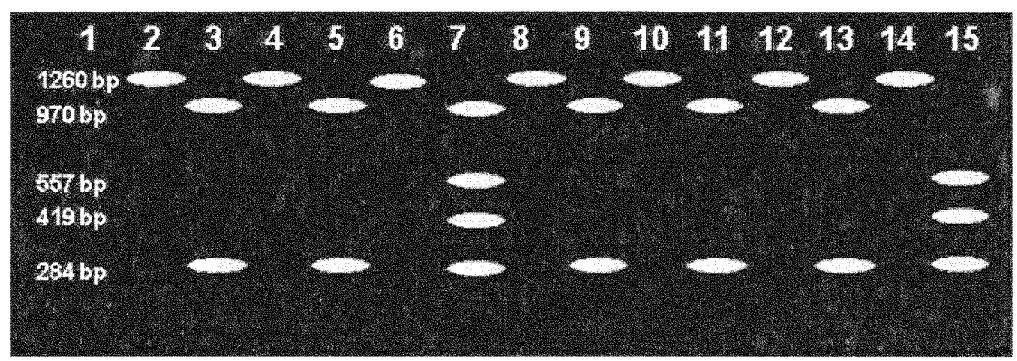

FIG. 9a: shows a schematically drawing of FIG. 9. The grey highlighted circles demonstrate the main signals of the FOR fragments as shown in FIG. 9.

Figure 10:
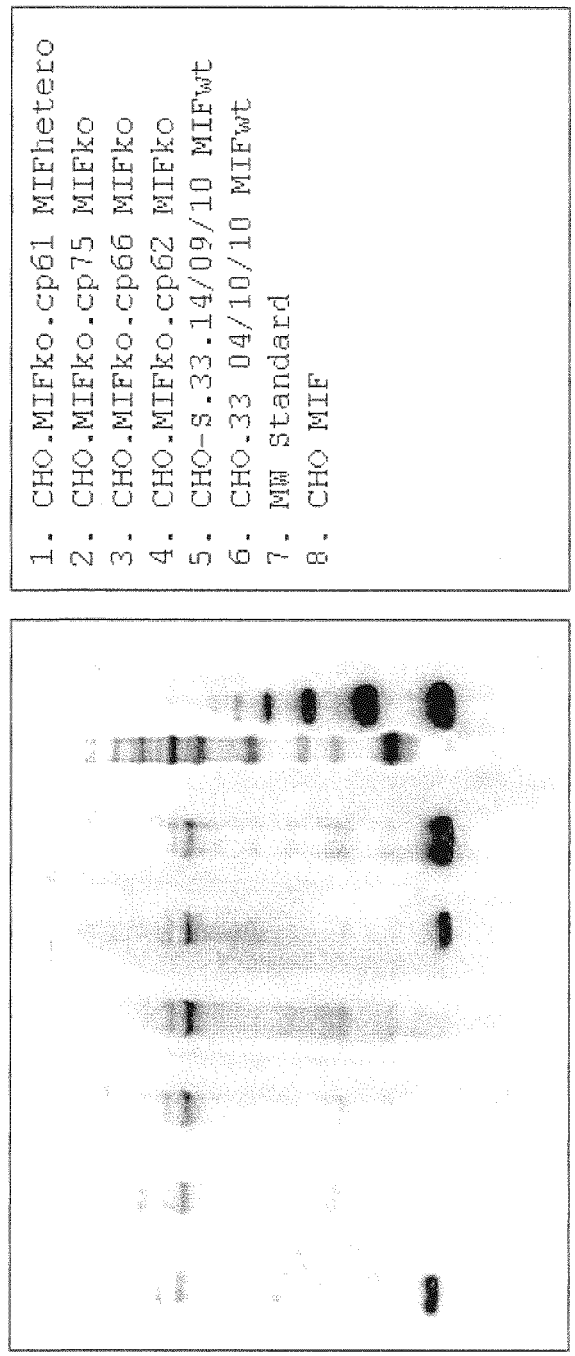

FIG. 10: is an example of a Western blot for the characterisation of CHO-MIF knockout cell lines producing antibody RAB0 on the protein level. Cell extracts of individual CHO-MIF heterozygous (lane 1), knockout (lanes 2-4) and wild-type (lane 5 & 6), cell clones are separated on a denaturing protein gel and transferred to a membrane. As a control, CHO-MIF purified from *E. coli* is on the gel (lane 8). The blot is stained using a MIF specific antibody. There is no MIF detectable in knockout cell clones (lanes 2, 3, 4).

Figure 10A:
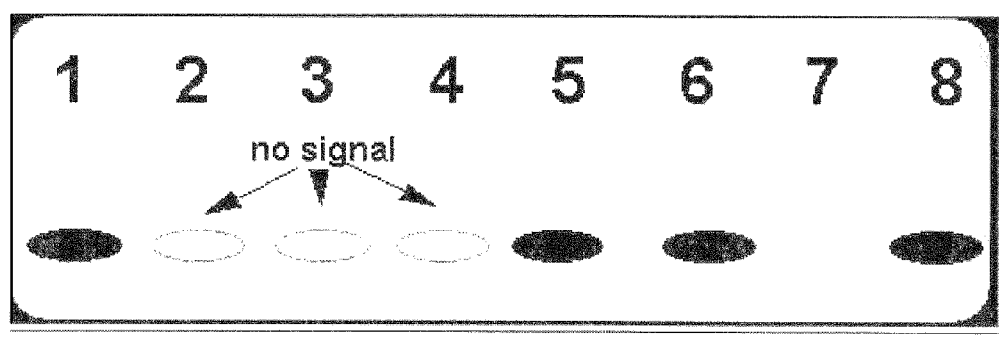

FIG. 10a: is a schematically drawing of FIG. 10. The dark circles demonstrate the positive CHO-MIF signals (lane 1, 5, 6, 8) of the Western blot; the highlighted open circles demonstrate the negative signals (lane 2, 3, 4) of CHO-MIF protein as shown in the Western blot in FIG. 10.

Figure 11:
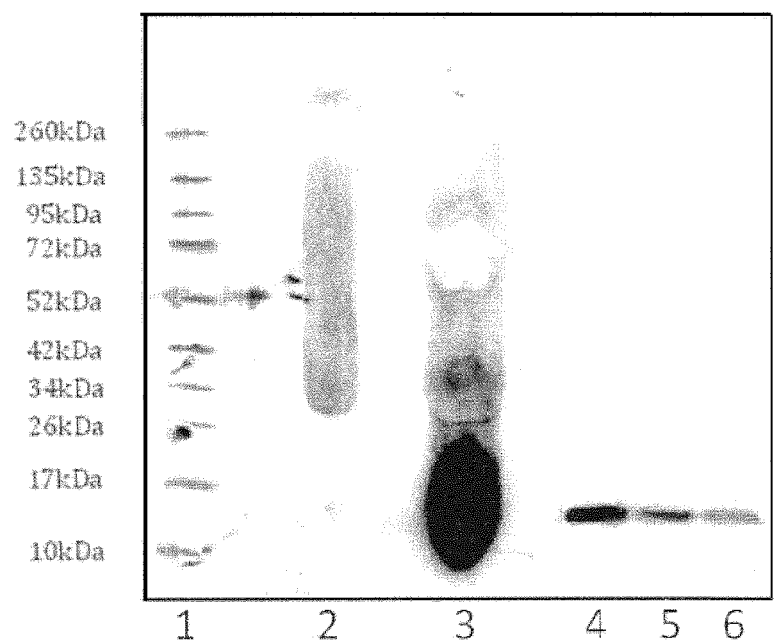

FIG. 11: is an example of a western blot analysis of a human anti-MIF antibody purified from a CHO-MIF knock-out cell line.

The MIF-specific antibody RAB0 is produced in a MIF knockout CHO cell line (lane 2) or in a wild type CHO cell line (lane 3). Even after loading the purified antibody up to 500 µg per lane on a gel there is no CHO-MIF detectable when the antibody is produced in the MIF knockout cell line. Different amounts of purified CHO-MIF produced in *E. coli* were applied as controls (lanes 4-6).

Figure 11A:
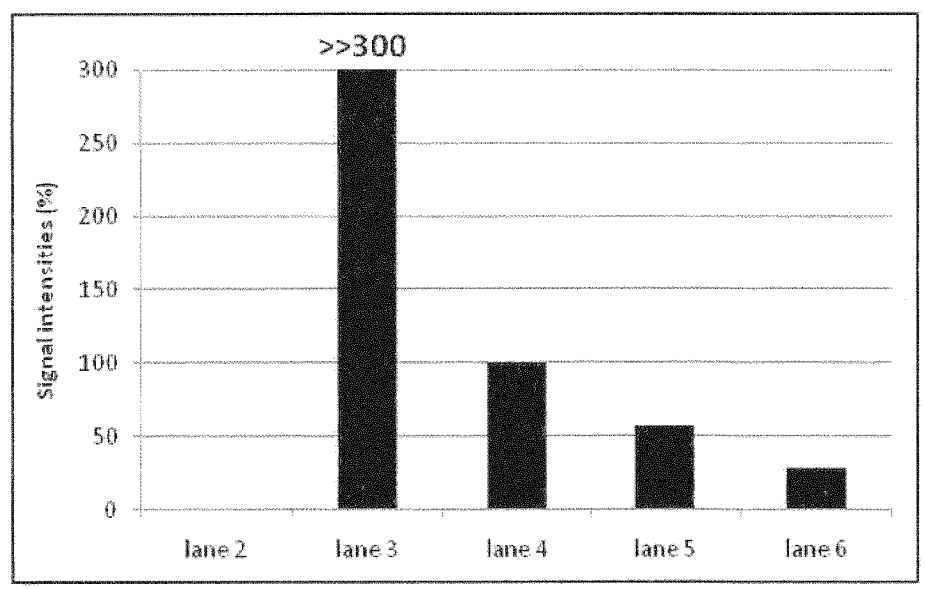

FIG. 11a: is a bar chart of the CHO-MIF protein signals resultant from a Western Blot as shown in FIG. 11. To that end, the CHO-MIF signals were scanned by a LAS4000 (Fujifilm Life Science®) using the Image Reader LAS4000 Scanner Software® and directly quantified by the Image Quant LAS4000® software. The 4 ng CHO-MIF signal from lane 4 was set to 100% and directly compared to the other CHO-MIF signals. 0% signal intensities for CHO-MIF was found in the purified anti MIF antibodies produced in knockout CHO cell line as shown in lane/bar 2; a huge signal (>>300%) of CHO-MIF was found in purified antibodies produced from wild-type CHO cell line shown in lane/bar 3; 57% of the 100% reference signal was found for the 2 ng CHO-MIF protein shown in lane/bar 5 and 28% signal intensities was found for 1 ng CHO-MIF as shown in lane/bar 5.

The present inventors have succeeded in identifying and characterizing the CHO-MIF gene. On that basis they further succeeded in the provision of tools and methods allowing production and testing of anti-MIF antibody preparations in CHO cells, which preparations are essentially free of contaminating CHO-MIF. These tools and methods further allowed production and testing of all preparations as produced in CHO cells, which comprise components which can be bound by CHO-MIF (i.e. CHO MIF binding proteins), whereupon these preparations are essentially free of contaminating CHO-MIF.

Thus, the present invention is directed to the analysis of the gene locus coding for CHO-MIF. This allows the generation of MIF knockout CHO cells producing recombinant antibodies, or other products, which can be bound by CHO-MIF, e.g. (CHO)MIF ligands, (CHO)MIF agonists or antagonists, (CHO)MIF inhibitors, like peptides binding (CHO)MIF, (CHO)MIF receptor fragments, preferably antibodies which are directed towards human MIF, essentially free of any CHO-MIF contaminants.

"Essentially without any CHO-MIF contamination" or "essentially free of CHO-MIF contamination", which are used interchangeably, in the context of this application shall mean that the amount of CHO-MIF is below 0.5 ppm. Preferably, the amount of CHO MIF is below 0.2 ppm.

The present invention is further directed to a knock-out cell line wherein the CHO-MIF gene is successfully knocked out, wherein this k.o. cell line shows essentially the same characteristics as the parenteral CHO wild type cell line.

The present invention is also directed to a highly sensitive method for the detection of ppm levels of CHO-MIF which during production in CHO cells of products which bind to CHO MIF, e.g. antibodies, preferably anti-MIF antibodies or antigen-binding fragments thereof can remain attached to the desired product in some cases. In a preferred embodiment, this detection method is based on the generation and purification of highly specific anti CHO-MIF antibodies which are affinity-purified polyclonal antibodies obtained from rabbits immunized with the CHO-MIF of the present invention. These antibodies are in a preferred embodiment generated by immunization with CHO-MIF produced by recombinant *E. coli* techniques.

The present invention is thus further directed to the isolation of mRNA coding for CHO-MIF as produced by CHO cells. The cDNA created by reverse transcription of this mRNA is cloned into a prokaryotic expression vector. The CHO-MIF protein expressed thereof in *E. coli* is purified to homogeneity. The recombinant CHO-MIF is used to immunize rabbits in order to generate the inventive polyclonal rabbit antibodies specific to CHO-MIF.

Very surprisingly, the affinity-purified polyclonal rabbit antibodies (see Example 4) as provided by the present inventors are capable of detecting CHO-MIF contaminations bound to the desired anti-MIF antibodies very sensitively; this enables the detection of these CHO-MIF contaminations down to the ppm range.

In a preferred embodiment, the detection step is carried out by a Western Blot analysis. Other analytical detection methods are, however, well known to a person skilled in the art, and include (though by no means limited to) e.g.

enzyme-linked immunoassays, radioimmunoassays, fluorescent immunoassays, bioluminescent and chemiluminescent immunoassays, competitive immunoassays, dot blot technology, and immune precipitation HPLC, mass spectrometry or LC/MS/MS.

Based on the knowledge of the CHO-MIF sequence, the present invention is further directed to the analysis of the gene locus coding for CHO-MIF. This allows the generation of MIF knockout CHO cells or the detection of CHO-MIF mRNA to verify the presence or absence of MIF in CHO cells. The inventors successfully provided a CHO MIF knock out cell line, wherein it is surprising that this cell line was stable and useful for the expression of recombinant proteins, particularly those which can bind CHO-MIF, preferably, antibodies, more preferred anti-MIF antibodies, in particular as MIF per se is involved in quite a few important cellular processes and its absence in a knock out cell should have disturbed the cellular processes to an extent where stable cell survival was not possible anymore.

Quite unexpectedly, the productivity for anti-MIF antibodies was however comparable to that as observed in the same cells without the knock out of CHO MIF (wild-type cells) (data not shown).

The antibodies as produced in the present inventive CHO MIF knock out cell lines are also comparable in their physico-chemical characteristics to those as produced in wild type cell lines (data not shown).

This invention is characterized particularly by the following features:
1. A method for the detection of CHO-MIF contaminations in a monoclonal anti-MIF antibody preparation, comprising the step of contacting the anti-MIF antibody preparation with a polyclonal anti-CHO-MIF antibody, affinity purified against CHO-MIF.
2. The method according to item 1 wherein the CHO-MIF contaminates a final CHO cell produced monoclonal anti-MIF antibody-preparation or a preparation of antigen-binding fragments thereof.
3. The method according to item 1 and/or 2 wherein the CHO-MIF is endogenous CHO-MIF produced by CHO cells.
4. The method according to any one or more of items 1 to 3 wherein the detection step is carried out by a semi-quantitative Western Blot analysis
5. Use of a rabbit anti-CHO-MIF polyclonal antibody, affinity purified against CHO-MIF, for the detection of CHO-MIF contaminations during production of monoclonal anti-MIF antibodies or antigen-binding fragments thereof or in the final preparation of monoclonal anti-MIF antibody or antigen-binding fragments thereof.
6. The use according to item 5 wherein the detection step is carried out as a semi-quantitative Western. Blot analysis.
7. A method for the production of anti-MIF antibodies or antigen-binding fragments thereof in CHO cells, wherein said antibodies or antigen-binding fragments thereof are essentially free of CHO-MIF, wherein a detection method as defined in any one of claims 1 to 6 is carried out.
8. A CHO-MIF knock-out CHO cell line.
9. The CHO-MIF knock-out CHO cell line, wherein the cell line comprises any one or more of the following (in *E. coli* deposited) plasmids: DSM 25110, DSM 25112, DSM 25111, DSM 25113, DSM 25114, DSM 25115, DSM 25859, DSM 25860, DSM 25861, DSM 25862, DSM 25863 and DSM 25864.
10. The CHO-MIF knock-out CHO cell line according to item 8 or 9, wherein the cell line comprises the plasmids DSM 25110 and DSM 25112 or DSM 25861 and DSM 25862.
11. The CHO-MIF knock-out CHO cell line according to item 8 or 9, wherein the cell line comprises the plasmids DSM 25111 and DSM 25113 or DSM 25859 and DSM 25860.
12. The CHO-MIF knock-out CHO cell line according to item 8 or 9, wherein the cell line comprises the plasmids DSM 25114 and DSM 25115 or DSM 25863 and DSM 25864.
13. The use of the CHO-MIF knock-out CHO cell line of any of items 8 to 12 for the production of a preparation of monoclonal anti-MIF antibodies or binding fragments thereof, preferably for the production of any one of antibodies RAB0, RAB9, RAB4, RAM0, RAM9 or RAM4.
14. Essentially CHO MIF free anti-MIF antibody preparation as obtainable by the method of item 7, or by use of the CHO-MIF knock-out cell line of any of items 8 to 12.
15. A method for the production of an essentially CHO MIF free anti-MIF antibody preparation which is characterized by the use of the CHO-MIF knock-out CHO cell line, according to any one of items 8-12.
16. Preparation of a recombinant MIF binding protein, preferably an (h)MIF binding protein, like an (h)MIF binding peptide, ligand, agonist, antagonist, inhibitor, or a MIF receptor fragment, or an anti-(h)MIF antibody preparation, produced in a CHO cell line, characterized in that said preparation is essentially free of CHO-MIF.
17. Preparation of a recombinant MIF binding protein, preferably an (h)MIF binding protein, like an (h)MIF binding peptide, ligand, agonist, antagonist, inhibitor, or a MIF receptor fragment, or an anti-(h)MIF antibody preparation, which is obtainable by the method according to item 15 or by a method of production which comprises, preferably as a quality control step, the method detection of any one of the above items 1-4 or 7.
18. Preparation of a recombinant MIF binding protein, preferably an (h)MIF binding protein, like an (h)MIF binding peptide, ligand, agonist, antagonist, inhibitor, or a MIF receptor fragment, or an anti-(h)MIF antibody preparation, produced by the method according to item 15 or by a method of production which comprises, preferably as a quality control step, the method of detection of any one of the above items 1-4 or 7.
19. The anti-hMIF antibody preparation of any of items 16-18 above, which is essentially free of CHO-MIF, wherein the anti-hMIF antibody is selected from the group of RAB4, RAB0, RAB9, RAM4, RAM0 and/or RAM9.

The plasmids as deposited for the above anti-hMIF antibodies are characterized by their DSM number which is the official number as obtained upon deposit under the Budapest Treaty with the German Collection of Microorganisms and Cell Cultures (DSMZ), Mascheroder Weg 1b, Braunschweig, Germany.

The plasmid with the DSM 25110 number comprises the light chain sequence of the anti-MIF antibody RAB4.

The plasmid with the DSM 25112 number comprises the heavy chain (IgG4) sequence of the anti-MIF antibody RAB4.

The co-expression of plasmids DSM 25110 and DSM 25112 in a suitable host cell, namely a CHO cell, results in the production of the preferred anti-MIF antibody RAB4.

The plasmid with the DSM 25111 number comprises the light chain sequence of the anti-MIF antibody RAB9.

The plasmid with the DSM 25113 number comprises the heavy chain (IgG4) sequence of the anti-MIF antibody RAB9.

The co-expression of plasmids DSM 25111 and DSM 25113 in a suitable host cell, namely a CHO cell, results in the production of the preferred anti-MIF antibody RAB9.

The plasmid with the DSM 25114 number comprises the light chain sequence of the anti-MIF antibody RAB0.

The plasmid with the DSM 25115 number comprises the heavy chain (IgG4) sequence of the anti-MIF antibody RAB0.

The co-expression of plasmids DSM 25114 and DSM 25115 in a suitable host cell, namely a CHO cell, results in the production of the preferred anti-MIF antibody RAB0.

Also deposited are antibodies RAM0, RAM9 and RAM4; all have been deposited with the DSZM, Braunschweig, Germany on Apr. 12, 2012 according to the Budapest Treaty, with the following designations:

RAM9—heavy chain: *E. coli* GA.662-01.pRAM9hc—DSM 25860.
RAM4—light chain: *E. coli* GA.906-04.pRAM41c—DSM 25861.
RAM9—light chain: *E. coli* GA.661-01.pRAM91c—DSM 25859.
RAM4—heavy chain: *E. coli* GA.657-02.pRAM4hc—DSM 25862.
RAM0—light chain: *E. coli* GA.906-01.pRAM01c—DSM 25863.
RAM0—heavy chain: *E. coli* GA.784-01.pRAM0hc—DSM 25864.

The production of anti-(ox)MIF antibodies may also include any method known in the art for the cultivation of said transformed cells, e.g. in a continuous or batchwise manner, and the expression of the anti-(ox)MIF antibody, e.g. constitutive or upon induction. It is referred in particular to WO 2009/086920 for further reference for the production of anti-(ox)MIF antibodies. In a preferred embodiment, the anti-(ox)MIF antibodies as produced according to the present invention bind to oxMIF or an epitope thereof. Particularly preferred antibodies in accordance with the present invention are antibodies RAB9, RAB4 and/or RAB0 as well as RAM9, RAM4 and/or RAM0.

The sequences of these antibodies are partly also disclosed in WO 2009/086920; see in addition the sequence list of the present application and the following:

```
for the amino acid sequence of the light chain
of RAB9:
                                          SEQ ID NO: 22
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC, for the amino acid seauence of the light chain
of RAB4:
                                          SEQ ID NO: 23
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC, for the amino acid sequence of the light chain
of RAB0:
                                          SEQ ID NO: 24
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC, for the amino acid sequence of the light chain
of RAE2:
                                          SEQ ID NO: 25
DIQMTQSPVT LSLSPGERAT LSCRASQSVR SSYLAWYQQK

PGQTPRLLIY GASNRATGIP DRFSGSGSGT DFTLTISRLE

PEDFAVYYCQ QYGNSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC, for the amino acid sequence of the heavy chain
of RAB9:
                                          SEQ ID NO: 26
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PCSRSTSEST AALGCLVKDY FPEPVTVSWN

SGALTSGVHT FPAVLQSSGL YSLSSVVTVP SSSLGTKTYT

CNVDHKPSNT KVDKRVESKY GPPCPPCPAP EFLGGPSVFL

FPPKPKDTLM ISRTPEVTCV VVDVSQEDPE VQFNWYVDGV

EVHNAKTKPR EEQFNSTYRV VSVLTVLHQD WLNGKEYKCK

VSNKGLPSSI EKTISKAKGQ PREPQVYTLP PSQEEMTKNQ

VSLTCLVKGF YPSDIAVEWE SNGQPENNYK TTPPVLDSDG

SFFLYSRLTV DKSRWQEGNV FSCSVMHEAL HNHYTQKSLS

LSLGK for the amino acid sequence of the heavy chain
of RAE4:
                                          SEQ ID NO: 27
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE
```

```
FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK
``` for the amino acid sequence of the heavy chain
of RAB0:
                                           SEQ ID NO: 28
```
EVQLLESGGG LVQPGGSLRL SCAASGFTFS WYAMDWVRQA

PGKGLEWVSG IYPSGGRTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK
``` for the amino acid sequence of the heavy chain
of RAB
                                           SEQ ID NO: 29
```
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK.
``` for the amino acid sequence of RAT0hc:
                                           SEQ ID NO: 30
```
EVQLLESGGG LVQPGGSLRL SCAASGFTFS WYAMDWVRQA

PGKGLEWVSG IYPSGGRTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK.
``` for the amino acid sequence of RAM01c:
                                           SEQ ID NO: 31
```
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
``` for the amino acid sequence of RAM9hc:
                                           SEQ ID NO: 32
```
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPELLGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLTCLV KGFYPSDIAV EWESNGQPEN NYKTTPPVLD

SDGSFFLYSK LTVDKSRWQQ GNVFSCSVMH EALHNHYTQK

SLSLSPGK.
``` for the amino acid sequence of RAM91c:
                                           SEQ ID NO: 33
```
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
``` for the amino acid sequence of RAM4hc:
                                           SEQ ID NO: 34
```
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED
```

```
-continued
PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK.

for the amino acid sequence of RAM41c:
                                    SEQ ID NO: 35
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
```

The anti-MIF antibody of the invention is preferably an isolated monoclonal antibody. The anti-MIF antibody can be an IgG, an IgM, an IgE, an IgA, or an IgD molecule. In other embodiments, the anti-MIF antibody is an IgG1, IgG2, IgG3 or IgG4 subclass. In other embodiments, the antibody is either subclass IgG1 or IgG4. In other embodiments, the antibody is subclass IgG4. In some embodiments, the IgG4 antibody has a single mutation changing the serine (serine-228, according to the Kabat numbering scheme) to proline. Accordingly, the CPSC sub-sequence in the Fc region of IgG4 becomes CPPC, which is a sub-sequence in IgG1 (Angal et al. Mol. Immunol. 1993, 30, 105-108).

Additionally, the production of anti-(ox)MIF antibodies may include any method known in the art for the purification of an antibody, e.g. via anion exchange chromatography or affinity chromatography. In one embodiment the anti-(ox) MIF antibody can be purified from cell culture supernatants by sire exclusion chromatography.

The terms "center region" and "C-terminal region" of MIF refer to the region of human MIF comprising amino acids 35-68 and aa 86-115, respectively, preferably aa 50-68 and aa 86 to 102 of human MIF, respectively.

Particularly preferred antibodies of the present invention bind to either region as 50-68 or region as 86-102 of human MIF. This is also reflected by the binding of the preferred antibodies RAB0, RAB4 RAB2 and RAB9 as well as RAM4, RAM9 and RAM0 which bind as follows:
RAB4 and RAM4: aa 86-102
RAB9 and RAM9: aa 50-68
RAB0 and RAM0: aa 86-102
RAB2: aa 86-102

The term "epitope" includes any protein determinant capable of specific binding to an immunoglobulin or an antibody fragment. Epitopic determinants usually consist of chemically active surface groupings of molecules such as exposed amino acids, amino sugars, or other carbohydrate side chains and usually have specific three-dimensional structural characteristics, as well as specific charge characteristics.

The following description of the production of anti-NIP antibodies shall illuminate exemplarily the process for producing a recombinant anti-MIF antibody preparation which process includes a step for testing whether the purified antibody preparation is free from contaminating MIF, i.e. detection step for CHO-MIF contaminations.

The production process according to the present invention of the anti-MIF antibodies includes any method for the generation of recombinant DNA by genetic engineering, e.g. via reverse transcription of RNA and/or amplification of DNA and cloning into expression vectors. In some embodiments, the vector is a viral vector, wherein additional DNA segments may be ligated into the viral genome. In some embodiments, the vector is capable of autonomous replication in a host cell into which it is introduced (e.g. bacterial vectors having a bacterial origin of replication and episomal mammalian vectors). In other embodiments, the vector (e.g. non-episomal mammalian vectors) can be integrated into the genome of a host cell upon introduction into the host cell, and thereby replicated along with the host genome. Moreover, certain vectors are capable of directing the expression of genes to which they are operatively linked. Such vectors are referred to herein as "recombinant expression vectors" (or simply "expression vectors").

Anti-MIF antibodies can be produced by means of conventional expression vectors, such as bacterial vectors (e.g. pBR322 and its derivatives), or eukaryotic vectors. Those sequences that encode the antibody can be provided with regulatory sequences that regulate the replication, expression and/or secretion from the host cell. These regulatory sequences comprise, for instance, promoters (e.g. CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors are constructed for the expression in cell cultures, namely in CHO cells.

The anti-MIF antibody light chain gene and the anti-MIF antibody heavy chain gene can be inserted into separate vectors or both genes are inserted into the same expression vector. The antibody genes are inserted into the expression vector by standard methods, e.g. ligation of complementary restriction sites on the antibody gene fragment and vector, or blunt end ligation if no restriction sites are present.

The production of anti-MIF antibodies or antigen-binding fragments thereof may include any method known in the art for the introduction of recombinant DNA into eukaryotic cells by transfection, e.g. via electroporation or microinjection. For example, the recombinant expression of anti-MIF antibody can be achieved by introducing an expression plasmid containing the anti-MIF antibody encoding DNA sequence under the control of one or more regulating sequences such as a strong promoter, into a CHO-cell line, by an appropriate transfection method resulting in cells having the introduced sequences stably integrated into the genome. The lipofection method is an example of a transfection method which may be used according to the present invention.

The production of anti-MIF antibodies may also include any method known in the art for the cultivation of said transformed cells, e.g. in a continuous or batchwise manner, and the expression of the anti-MIF antibody, e.g. constitutive or upon induction. It is referred in particular to WO 2009/086920 for further reference for the production of anti-MIF antibodies. In a preferred embodiment, the antibodies of the CHO-MIF free anti-MIF antibody preparation as produced according to the present invention bind to MIF or a MIF fragment. Particularly preferred antibodies to be produced in accordance with the present invention are RAB9, RAB4 and RAB0 (deposited as *E. coli* containing plasmids DSM 25114 and DSM 25115 for RAB0, DSM 25111 and DSM 25113 for RAB9 and DSM 25110 and DSM 25112 for RAB4, respectively).

The host cell type, which is used in the production method for the production of MIF, as described herein, is a CHO cell. In one embodiment, the anti-MIF antibody is expressed in a DHFR-deficient CHO cell line, e.g. DXB11, and with the addition of G418 as a selection marker. When recombinant expression vectors encoding antibody genes are introduced into CHO host cells, the antibodies are produced by culturing the host cells for a period of time sufficient to allow for expression of the antibody in the host cells or secretion of the antibody into the culture medium in which the host cells are grown.

Anti-MIF antibodies can be covered from the culture medium using standard protein purification methods.

Additionally, the production of anti-MIF antibodies may include any method known in the art for the purification an antibody, e.g. via anion exchange chromatography or affinity chromatography. In one embodiment the anti-MIF antibody can be purified from cell culture supernatants by size exclusion chromatography.

The present invention now provides an advantageous method which clearly allows to improve and optimize the prior art methods for the production of anti-MIF antibodies or antigen-binding fragments thereof.

In particular, the present inventors were the first to show that antibody preparations prepared with CHO cells could comprise CHO-MIF contaminations which would render the final preparation useless for pharmaceutical or research purposes.

The present inventors were then the first to identify and characterize the CHO-MIF gene. Based on this knowledge, the inventors here additionally provide a specific detection method which allows the detection of a CHO-MIF contamination bound to anti-MIF antibodies, down to the ppm range.

Very surprisingly, the present invention thus provides for the possibility of verifying that the production process for anti-MIF antibodies, in particular the purification process, is suitable for generating a preparation essentially free of CHO-MIF. This is the prerequisite to establish a production method for the preparation of anti-MIF antibodies free of CHO-MIF. In particular, this improvement allows the optimization and combination of methods known in the art for purification of the antibody preparations in a manner which depletes the CHO-MIF contaminants, thus allowing the provision of a highly pure final Ab-preparation, which is free of CHO-MIF contaminations. In addition, the inventive method is a highly sensitive detection method for said contaminations is a safeguard in the industrial production process, ensuring that a highly pure final Ab-preparation, which is free of CHO-MIF contaminations, is produced. Preferably, this detection is carried with a detection step that uses a polyclonal rabbit anti-MIF antibody that has been obtained by affinity purification against CHO-MIF. Affinity purification is carried out as well known to a person skilled in the art and described e.g. in Lottspeich F. and Zorbas H. (1998) Bioanalytik, Spektrum Akademischer Verlag Heidelberg-Berlin, ISBN 3-8274-0041-4.

The CHO-MIF contaminations can be detected down to ppm-level, in particular it is possible to detect CHO-MIF contaminations down to 0.5 ppm (corresponding to 0.25 ng CHO-MIF in 500 µg antibody preparation) using a highly sensitive rabbit anti CHO-MIF antibody in a common Western Blot technology quantified by a chemiluminescence signal in a digital quantitative imaging system (e.g. ImageQuant LAS 4000 from GE Healthcare).

"CHO-MIF contamination" in this context means CHO-MIF bound to a recombinantly produced product, e.g. to anti-MIF antibodies in a preparation of a recombinantly produced product, e.g. anti-MIF antibodies.

The high sensitivity of the present detection method is possible particularly with the polyclonal rabbit anti-MIF antibodies obtained by affinity purification.

In a further alternative embodiment of producing MIF-free anti-MIF antibodies in CHO cells, the present invention is directed to knock-out CHO cell lines which do not produce CHO-MIF. With these knock-out cell lines it is possible to carry out a production method which provides an extremely pure anti-MIF antibody preparation which is essentially free of CHO-MIF contaminations.

In a preferred embodiment, the above described detection method can be used for quality control of a protein produced recombinantly in a CHO MIF cell line, preferably an anti-MIF antibody production, in particular to ensure that the final preparation is essentially free of CHO MIF. The detection method can also be used for a quality control of CHO MIF knock out cell lines.

Knock-out cells according to the present invention can be produced according to methods known in the art, whereby one possibility is described below in the examples in detail though the invention should not be construed to be limited to this embodiment.

EXAMPLES

Example 1

Determination of the DNA Sequence Encoding CHO-MIF

Oligonucleotides annealing to the 5' end and the 3' end of the coding region of CHO-MIF were designed by comparing DNA sequences of related species. Highly conserved areas were selected to design oligonucleotides 8951 and 8954 containing wobble bases, to ensure binding to their corresponding region in the CHO-MIF DNA. Using these oligonucleotides together with a polyT oligo it was possible to amplify a cDNA copy from mRNA isolated from CHO cells with standard cDNA cloning procedures. The resulting PCR product was subjected to DNA sequencing.

After knowing the DNA sequence of the CHO-MIF cDNA it was possible to design specific primers for the amplification of fragments from the genomic DNA purified from CHO cells using standard procedures. Three genomic fragments in the area of the cDNA were amplified by PCR and the following PCR products were achieved:

P27463 with primers 9063 and 9196, sequenced with oligos 9063, 9196;
P27465 using primers 9199 and 9064, sequenced with 9064;
P28254 with primers 9216 and 9244, sequenced with 9216, 9242.

To verify the sequence around the ATG start codon and the 5' upstream region, the genomic DNA of CHO cells was digested with BstHI and circularized. BstHI was known from the cDNA sequence to cut 140 bp downstream of the ATG in the cDNA. The circularized DNA was amplified by inverse PCR using two specific oligonucleotides 9216 (reverse primer) and 9242 (direct primer) binding in the already known part of the cDNA. Using this PCR product (P27883)

the sequence of the genomic DNA several hundred base pairs upstream the ATG could be determined.

The DNA and corresponding protein sequence of CHO-MIF are shown in FIG. 1 and SEQ ID No: 1 and 2.

Sequences of Oligonucleotides (primers) used to amplify and sequence the CHO-MIF cDNA:

```
pPCR.MIFspec(1)-8951:
                                          (SEQ ID NO: 3)
ATGTTCRTSGTRAACACCAAYGT pPCR.MIFspec(4)-8954:
                                          (SEQ ID NO: 4)
GCGAAGGTGGARYYGTTCCAG pPCR.choMIF(1)-9063:
                                          (SEQ ID NO: 5)
TGACTTTTAGCGGCTCTAGCGAC pPCR.choMIF(2)-9064:
                                          (SEQ ID NO: 6)
GATGTGCAGGCGATCAGCCA pPCR.choMIF-9196:
                                          (SEQ ID NO: 7)
ATTTCTCCCGATCGGAAGGTGG pPCR.choMIF-9216:
                                          (SEQ ID NO: 8)
GGTGAGCTCGGAGAGAAGC pPCR.choMIF-9242:
                                          (SEQ ID NO: 9)
CGGCCCAGTACATCGCAGT pPCR.choMIF-9244:
                                          (SEQ ID NO: 10)
GCTGCACGCAGCGTTCTGTT pPCR.choMIFg-9983:
                                          (SEQ ID NO: 11)
CGTTAATCTGCAGCGTCTACCTGA pPCR.choMIFg-9879:
                                          (SEQ ID NO: 12)
GTAAGGCCACTATAGGAAAGCCTG pPCR.choMIF-9199:
                                          (SEQ ID NO: 13)
GCTTCTCTCCGAGCTCACC
```

Example 2

Identification and Characterization of the CHO-MIF Gene Locus

The experimental strategy leading to the DNA sequence of CHO-MIF cDNA and genomic DNA is described in example 1. The analysis of cDNA and genomic DNA was carried out simultaneously.

The overall organization of the gene locus was determined by aligning genomic and cDNA sequences. The coding region of CHO-MIF is fragmented on three exons interrupted by two short introns. The sequence of the CHO-MIF gene locus is shown in FIG. 2.

Example 3

Production and Purification of Recombinant CHO-MIF

Figure 3:
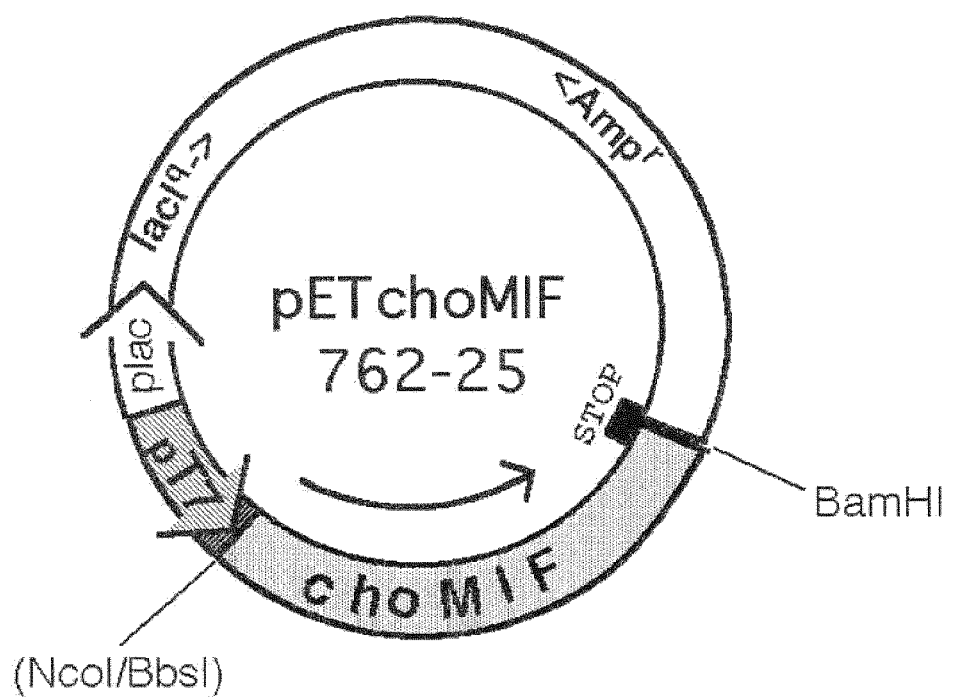
FIG. 3: is a schematic drawing of the *E. coli* expression plasmid pETchoMIF 762-25 based on the pET19b vector (Novagen). The complete cDNA of CHO-MIF is inserted behind the T7 promoter and transcribed by the T7 polymerase, which is part of the *E. coli* BL21 host strain.

The cDNA of CHO-MIF was cloned into the *E. coli* expression vector pET19b (Novagen) under the control of the T7 promoter. The plasmid is shown in FIG. 3.

The plasmid was transformed in *E. coli* strain BL21-CodonPlus (DE3)-RP (Stratagene). This strain contains a stably inserted copy of the RNA-polymerase of the bacteriophage T7 under the control of the IPTG inducible lac promoter. The CHO-MIF protein was expressed to high levels after induction with IPTG and highly purified using a 2 step purification protocol: First the sample was applied to an anion exchange DEAE-Sepharose column (buffer A: 20 mM Tris/HCl, pH 7.8; buffer B: 20 mM Tris/HCl, pH 7.8 including 1 M NaCl; recombinant CHO-MIF eluates by a linear gradient at 10% buffer B). In the second step the protein was loaded onto a Source S column (buffer A: 20 mM BisTris/HCl, pH 5.5; buffer B: 20 mM BisTris/HCl, pH 5.5 including 1 M NaCl; recombinant CHO-MIF eluates by a linear gradient between 7-10% buffer B). Finally the protein was concentrated and re-buffered in PBS using common desalting columns (e.g. PD-10 columns). The purity of CHO-MIF was confirmed after gel electrophoresis procedure by Coomassie staining.

Example 4

Detection of ppm Levels of CHO-MIF Contaminations in an Anti-MIF Antibody Preparation A highly sensitive semi-quantitative Western Blot analysis was established to monitor CHO-MIF contaminations in recombinant anti MIF antibody preparations that allow the detection of ppm levels of CHO-MIF.

Purified recombinant CHO-MIF expressed in *E. coli* was used to immunize rabbits in order to generate specific antibodies against CHO-MIF. Specific rabbit anti CHO-MIF antibodies were purified by a two-step purification (see a) and b) below). The resultant specific rabbit anti CHO-MIF antibodies enabled a highly sensitive semi-quantitative Western Blot method that allowed the detection of the CHO-MIF contaminant in a lower picogram range. This allows a CHO-MIF impurity monitoring during the downstream process of human anti-MIF antibodies produced in CHO-cells (FIGS. 4, 4a, 5 and 5a).

The detection limit of CHO-MIF impurities in human anti-MIF antibodies was determined with 0.25 ng/lane which is corresponding to 0.5 ppm in 500 µg human anti-MIF antibody preparation (shown in FIGS. 7 and 7a).

a) Immunization of Rabbits by Recombinant CHO-MIF.

To generate CHO-MIF specific antibodies, 10 rabbits were immunized according to the following protocol. For the initial immunization: 25 µg of recombinant CHO-MIF (in 100 µl PBS) were mixed with 100 µl CFA (Complete Freund's Adjuvant). The animals received subcutaneously 200 µl (4×50 µl) of the mixture. Two boost immunizations were performed in 2-3 weeks intervals with the same dose per animal as described above using IFA (Incomplete Freund's Adjuvant). Sera were tested by ELISA. Two weeks after the second boost, the rabbits were exsanguinated after narcotization by Pentobarbital. Sera were pooled for the isolation of the anti CHO-MIF antibodies.

b) Purification of Total CHO-MIF Immunized Rabbits.

The purification was achieved by affinity chromatography using protein A MabSelect Sure affinity material from GE Healthcare. Typically, serum from CHO-MIF immunized rabbits was diluted 1:2 in buffer A (=20 mM Na$_2$HPO$_4$, pH 7.0) and applied to a 100 ml MabSelect Sure column. Unbound or unspecific serum material was washed out by a 10 column volume's (CV) washing procedure with buffer A and the elution of total rabbit IgG was done by a pH shift using a 100% gradient step to buffer B (100 mM glycine, pH 2.8). The elution fractions were pooled and re-buffered in 20 mM Na$_2$HPO$_4$ pH 7.0 for the next affinity purification step.
c) Purification of CHO-MIF Specific Antibodies.

Figure 4:
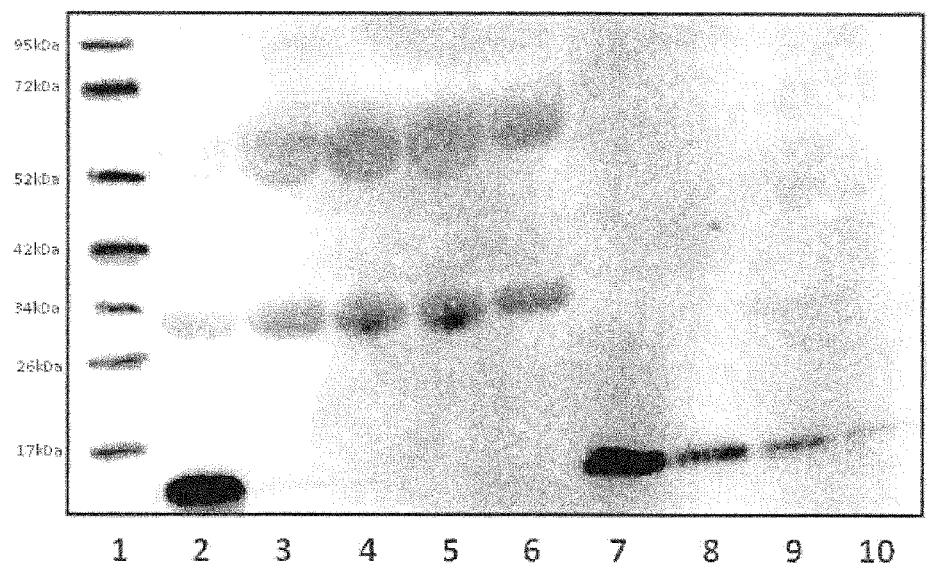
FIG. 4: is a Western Blot of CHO-MIF detection from anti-MIF antibodies resultant from different downstream process steps. The Blot was detected by the specific affinity purified rabbit anti CHO-MIF antibody and a commercial available horse radish peroxidase conjugated donkey anti rabbit IgG. Lane 1: molecular weight protein marker; Lane 2: 50 µg of anti-MIF antibody fractions before removal of CHO-MIF impurity; Lane 3-5: each 50 µg of anti-MIF antibody fractions from different downstream process steps; Lane 6: 50 µg of anti-MIF antibody fraction after removal of CHO-MIF impurities; Lane 7-10: recombinant CHO-MIF reference 4 ng, 2 ng, 1 ng and 0.5 ng/lane.
Figure 4A:
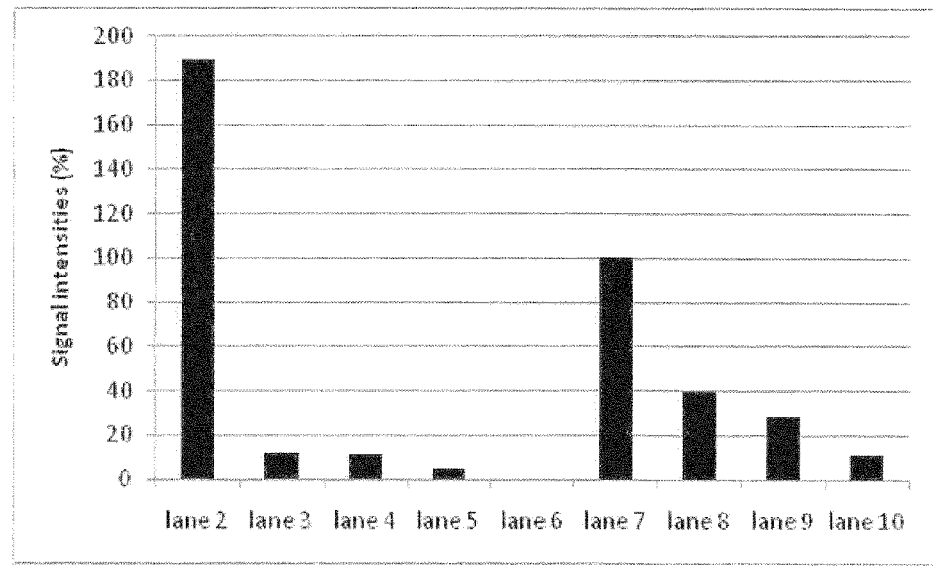
FIG. 4a: is a bar chart of the CHO-MIF protein signals resultant from a Western Blot as shown in FIG. 4. To that end, the CHO-MIF signals were scanned by a LAS4000 (Fujifilm Life Science®) using the Image Reader LAS4000 Scanner Software® and directly quantified by the Image Quant LAS4000® software. The 4 ng CHO-MIF signal from lane 7 was set to 100% and directly compared to the other CHO-MIF signals; 189% signal intensity was found for the CHO-MIF impurity in 50 µg anti MIF antibodies resultant after the first step of the downstream process as shown in lane/bar 2; 12% signal intensity was found for the CHO-MIF impurity in 50 µg anti MIF antibodies resultant after the second step of the downstream process as shown in lane/bar 3; 11% signal intensity was found for the CHO-MIF impurity in 50 µg anti MIF antibodies resultant after the third step of the downstream process as shown in lane/bar 4; 5% signal intensity was found for the CHO-MIF impurity in 50 µg anti MIF antibodies resultant after the fourth step of the downstream process as shown in lane/bar 5; 0% signal intensity was found for the CHO-MIF impurity in 50 µg anti MIF antibodies resultant after the last step of the downstream process as shown in lane/bar 6; 40% signal intensity was calculated for 2 ng recombinant CHO-MIF as shown in lane/bar 8; 29% signal intensity was calculated for 1 ng recombinant CHO-MIF as shown in lane/bar 9; 11% signal intensity was calculated for 0.5 ng recombinant CHO-MIF as shown in lane/bar 10.
Figure 5:
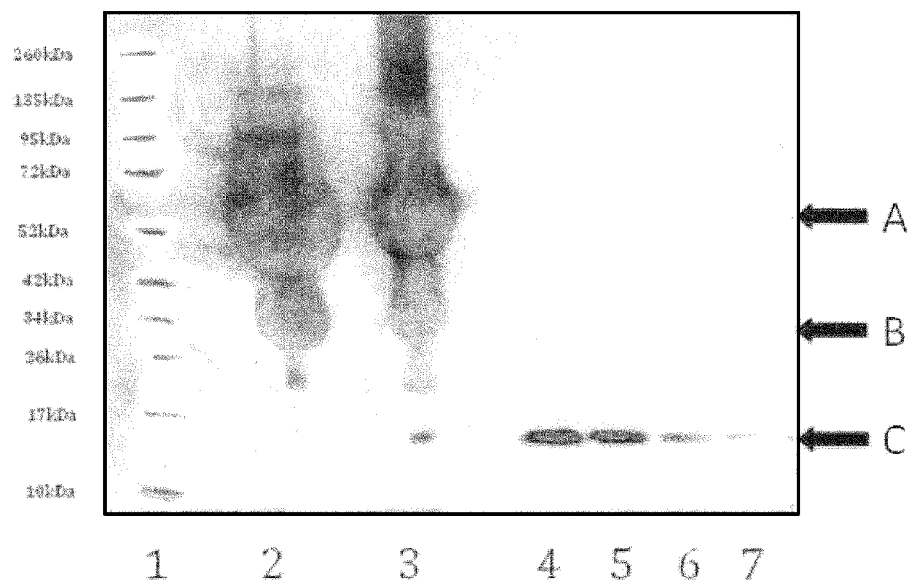
FIG. 5: is a Western Blot for quantification of CHO-MIF impurities in finalized anti-MIF production lots. The Blot was detected by the specific affinity purified rabbit anti CHO-MIF antibody and a commercially available horse radish peroxidase conjugated donkey anti rabbit IgG. Lane 1: molecular weight protein marker; Lane 2: final purified anti-MIF antibodies after removal of CHO-MIF contaminants (500 µg anti-MIF antibodies/lane); Lane 3: 500 µg final purified anti-MIF antibodies but spiked with 1 ng CHO-MIF; Lane 4-7: recombinant CHO-MIF reference, 4 ng/lane (corresponding to 8 ppm in 500 µg anti-MIF antibodies), 2 ng/lane (corresponding to 4 ppm in 500 µg anti-MIF antibodies), 1 ng/lane (corresponding to 2 ppm in 500 µg anti-MIF antibodies) and 0.5 ng/lane (corresponding to 1 ppm in 500 µg anti-MIF antibodies). Arrow A denotes the heavy chain of the anti-MIF antibody sample, arrow B the light chain of the anti-MIF antibody sample and arrow C denotes the CHO-MIF bands.
Figure 5A:
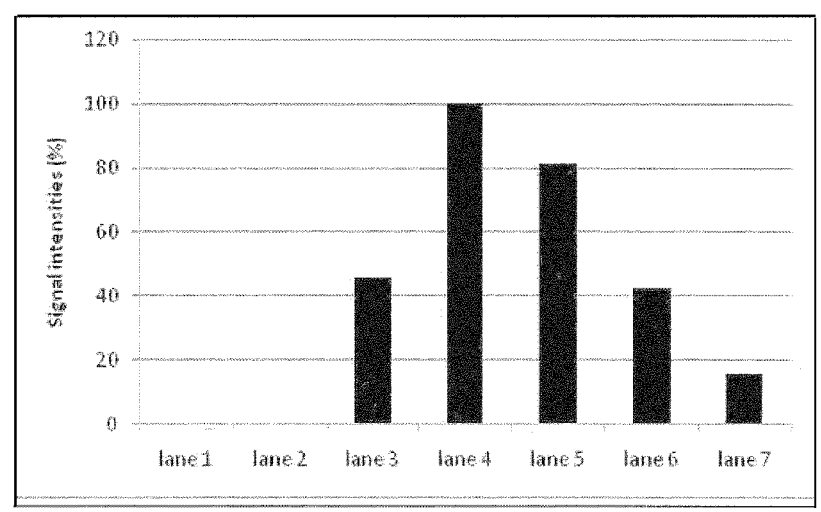
FIG. 5a: is a bar chart of the CHO-MIF protein signals resultant from a Western Blot as shown in FIG. 5. To that end, the CHO-MIF signals were scanned by a LAS4000 (Fujifilm Life Science®) using the Image Reader LAS4000 Scanner Software® and directly quantified by the Image Quant LAS4000® software. The 4 ng CHO-MIF signal from lane 4 was set to 100% and directly compared to the other CHO-MIF signals. No CHO-MIF signals were found for the marker protein added on lane 1 as well as for the final purified anti MIF antibody preparation shown in lane/bar 1 and 2.46% of the 100% reference signal was found for the purified anti MIF antibody spiked with 1 ng recombinant CHO-MIF as shown in lane/bar 3; 81% of the 100% reference signal was found for the 2 ng CHO-MIF protein shown in lane/bar 5; 42% of the 100% reference signal was found for the 1 ng CHO-MIF protein shown in lane/bar 6; 16% of the 100% reference signal was found for the 0.5 ng CHO-MIF protein shown in lane/bar 7.

Affinity purified rabbit anti CHO-MIF antibodies were finally purified by a self prepared 5 ml NHS-column (GE Healthcare) coupled with recombinant CHO-MIF. Typically, 100 ml fractions of the re-buffered total rabbit IgG was applied to a 5 ml CHO-MIF affinity column. After a washing step (20 CV with buffer A) the elution of the specific anti CHO-MIF antibodies was achieved by a pH shift using a 100% gradient step to buffer B (100 mM glycine, pH 2.8). Eluted material was pooled, re-buffered in PBS, concentrated if necessary and stored at −80°. Functionality of the purified rabbit anti-CHO-MIF antibodies was proved by Western Blot and CHO-MIF ELISA.

d) Detection of CHO-MIF in a Monoclonal Anti-MIF Antibody Preparation.
Test Principle Antibody samples of interest were separated by SDS-PAGE electrophoresis (sodium dodecyl sulphate-polyacrylamide-gel electrophoresis) and transferred to a commonly used membrane e.g. polyvinylidene fluoride (PVDF) or nitrocellulose. The target protein CHO-MIF was identified and quantified by the specific polyclonal rabbit anti CHO-MIF antibody and chemiluminescence reaction using a corresponding secondary antibody conjugate.
Preparation of Samples and Controls to Monitor Downstream Process:

To monitor the removal of contaminating CHO-MIF during the purification of anti-MIF antibodies, samples were diluted with SDS buffer to a defined concentration. All samples had the same concentration before they were loaded on the gel (recommended: 30-80 µg anti-MIF antibody/lane) (FIGS. 4 and 4a).

The controls (recombinant CHO-MIF) were also loaded on the SDS gel at a final concentration of 0.5, 1, 2 and 4 ng/lane.

Preparation of Samples and Controls to Analyze the Final Purified Antibodies

For analysis of potential CHO-MIF contamination in final purified anti-MIF antibody preparations, 500 µg/lane were loaded on the SDS Page. The controls (recombinant CHO-MIF) were added to the gel at a final amount of 0.5, 1, 2 and 4 ng/lane. (FIGS. 5 and 5a)
Test Details Samples were diluted 1:1 in SDS buffer (100 mM Tris, 4% SDS, 0.2% bromophenol blue, 20% glycerin, 200 mM DTT, pH 6.8) and incubated for 5 minutes at 99° C. (protein reduction and denaturation step). Afterwards, a defined concentration of each sample was loaded on a 4-12% Bis/Tris Gel (Invitrogen) and separated by gel electrophoresis with subsequent electrotransfer to a suitable membrane (e.g. PVDF). For the reduction of unspecific binding effects the membrane was blocked by 2% dry milk diluted in TBST buffer (25 mM Tris, 150 mM NaCl, 0.1% polysorbate 20, pH 7.5) for 2 hours at RT. Removal of unbound proteins was achieved by washing steps again with TBST. The detection of CHO-MIF was done by affinity purified rabbit anti CHO-MIF antibodies diluted in 0.05% dry milk dissolved in TBST. A secondary antibody conjugated with horseradish peroxides (e.g. donkey anti rabbit/HRP) was incubated with the membrane for 1 hour at RT and washed again with TBST. The specific CHO-MIF signal was detected and quantified by addition of a chemiluminescence substrate (e.g. Super Signal West Femto, Pierce) using a Luminescent Image Analyzer from Fujifilm (LAS-4000).

Example 5

Highly Sensitive Detection of CHO-MIF by Affinity Purified Rabbit Anti CHO-MIF Antibodies The sensitivity of the affinity purified rabbit anti CHO-MIF antibodies to CHO-MIF was compared to two other affinity purified polyclonal antibodies directed against human MIF and mouse MIF. These polyclonal antibodies were also produced by the same procedure as described for the rabbit anti CHO-MIF antibodies, with the following exception: rabbit anti huMIF was affinity purified against rhuMIF and rabbit anti moMIF was affinity purified against rmoMIF (same conditions as described for rabbit anti CHO-MIF antibodies).

Different amounts of CHO-MIF (2, 1 and 0.5 ng/lane) were applied to an SDS gel, separated by a common electrophoresis procedure and blotted to a PVDF membrane. To compare the sensitivity of each polyclonal rabbit anti-MIF antibody to OHO-MIF, they were applied to the Western Blots at the same concentration (each 3.5 µg/mL). The functionality of the rabbit anti human and mouse MIF antibodies were additionally proved by a positive sample (10 ng huMIF and 10 ng moMIF).

Figure 6:
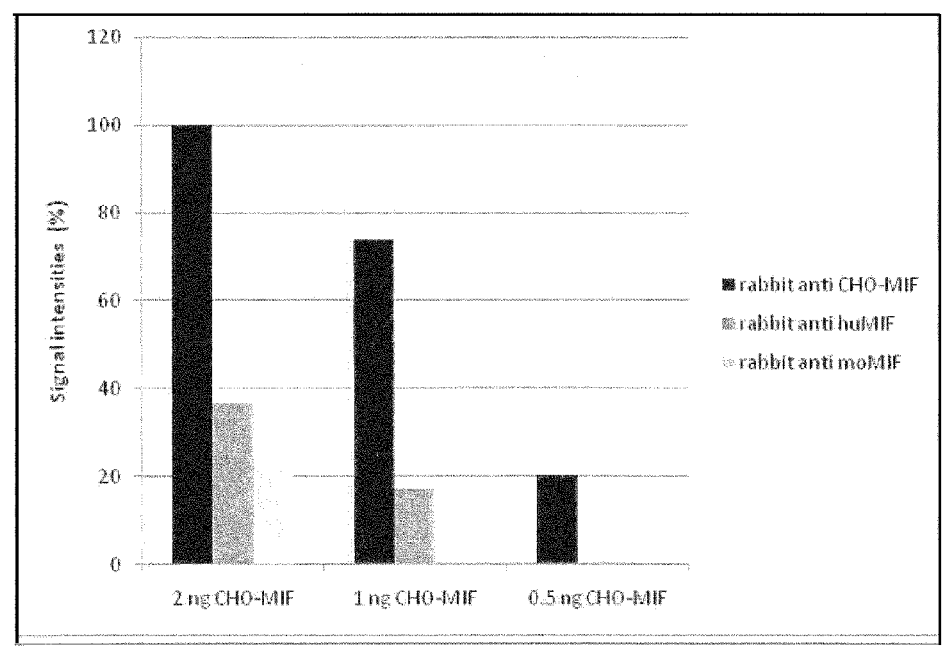
FIG. 6: is a bar chart of CHO-MIF proteins resultant from Western Blots detected by different rabbit anti MIF antibodies (data not shown). The bars demonstrate the highest sensitivity of affinity purified rabbit anti CHO-MIF antibodies to CHO-MIF in contrast to rabbit anti huMIF and rabbit anti moMIF antibodies. To that end, to each Western Blot the same amount of CHO-MIF proteins were blotted (2 ng/lane; 1 ng/lane; 0.5 ng/lane) and the resultant signal intensities of the CHO-MIF electronically compared by a LAS4000 (Fujifilm Life Science®). Each Western Blot was detected with the same amount of the respective rabbit antibodies (3.5 µg/mL) in combination with a horse radish peroxidase conjugated donkey anti-rabbit IgG (1:6000). The Western Blots detected by rabbit anti huMIF and rabbit anti moMIF were additionally controlled by 10 ng rhuMIF or 10 ng rmoMIF to demonstrate the functionality of both antibody preparations (data not shown). Afterwards, the resultant CHO-MIF signals were scanned by a LAS4000 Image Reader LAS4000 Scanner Software® and directly quantified by the Image Quant LAS4000® software. For the directly comparison of all CHO-MIF signals, the 2 ng CHO-MIF signal from the rabbit anti CHO-MIF antibody blot was set to 100%. Black bars: CHO-MIF signals resultant from the rabbit anti CHO-MIF antibodies; dark grey bars: CHO-MIF signals resultant from the rabbit anti huMIF antibodies; light grey bars: CHO-MIF signals resultant from the rabbit anti moMIF antibodies.

As shown in FIG. 6, the highest sensitivity for CHO-MIF was found for the affinity purified rabbit anti CHO-MIF antibodies (see black arrow, FIG. 6).

The lowest concentration of CHO-MIF detected by rabbit anti CHO-MIF antibody was determined with the 0.25 ng/lane which is corresponding to 0.5 ppm in 500 µg human anti-MIF antibody preparation (shown in FIG. 7).

Example 6

Generation of MIF Knock Out CHO Cell Lines

The exact knowledge of the genomic structure including exon/intron junctions of a gene locus is a prerequisite for the design of a Zinc finger nuclease (ZFN) (Sangamo-Sigma Aldrich). The genomic organization of the CHO-MIF gene locus was determined in example 2. The nuclease was designed to create a double strand break at the exon1/intron1 junction. (FIG. 8). The advantage of the ZFN technology is that both alleles of a gene can be knocked out in a single step with a very high frequency. A MIF knockout cell line was generated and the absence of MIF was demonstrated by genetic characterization (FIGS. 9 and 9a) and Western Blot analysis (FIGS. 10 and 10a) using the CHO-MIF specific antibodies described in Example 4. This cell line was used for the expression of anti-MIF antibodies avoiding the problems associated with the binding to its cellular target.
a) Generation of Unique MIF Knockout Cell Clones.

A CHO cell line stably expressing the anti-MIF antibody RAB0 (RAB0.CHO-S.33) was transfected with two plasmids expressing both subunits of the specific ZFN. Under these conditions a functional nuclease is expressed destroying the endogenous MIF locus in the cellular genome. Two weeks after transfection the cell pool was diluted in semi-solid medium. After growth for 1 week unique colonies were transferred to 96 well plates using the ClonePix (Genetix Limited) and grown up to small cultures.

Using the same strategy the endogenous MIF was knocked out in different CHO host cell lines like CHO-S and CHO-DG44.

b) Genetic Characterization of MIF Knockout RAB0 Producing CHO-S Cell Lines.

The chromosomal DNA of unique cell clones was purified using the QIAamp DNA Mini Kit (50) form Qiagen according to the manufacturer's protocol. Using the DNA as a template a specific fragment was amplified by PCR using the following primers: pPCR.choMIFg 9983: CGTTAATCT-GCAGCGTCTACCTGA (SEQ ID NO: 11) and pPCR-.choMIFg 9879 GTAAGGCCACTATAGGAAAGCCTG (SEQ ID NO: 12).

In case of a wild-type (wt) cell clone the expected fragment is 1260 bp long (FIG. 8). In case of knockout cell lines the length is varying depending on the individual structure of the mutated gene. Usually nucleotides are deleted or inserted at the cleavage site of the ZEN. At the same time a recognition site of the restriction enzyme NaeI overlapping the ZFN cleavage site is destroyed.

The PCR products were cleaved with NaeI and the fragments were separated on a 1% agarose gel. Due to the loss of the restriction site in knockout cell lines an altered restriction pattern is expected (FIGS. 9 and 9a).

c) Western Blot Analysis of MIF Knockout RAB0 Producing CHO-S Cell Lines

To prove the depletion of MIF protein of MIF, knockout cell protein extracts were analyzed by western blots.

Cell extracts were prepared using a commercially available lysis buffer (#9803 "Cell Signaling"). The samples were separated on an Invitrogen NU Page 4-12% Bis/Tris-Gel 1,5 mm×15 well and transferred to a nitrocellulose membrane. CHO-MIF was detected by indirect immunofluorescence using a polyclonal rabbit anti-MIF antibody as described in Example 5 as first antibody and anti-rabbit IgG, horseradish peroxidase from Invitrogen as second antibody. The protein pattern was visualised using a Luminescent Image Analyser CB-SG-39 (FIGS. 10 and 10a).

Example 7

Production of Antibody in CHO-MIF Knockout Cell Line

Anti-MIF antibody RAB0 was produced in a CHO cell line after knock out of the endogenous CHO-MIF. In comparison, the same antibody was produced in a CHO wildtype MIF cell line. The antibody was purified on a Protein A column without any further treatment to remove the CHO-MIF bound to the antibody. The purified antibody was characterized by Western blot analysis as described in Example 4d. There was no remaining CHO-MIF detectable in the knockout cell line CHO-RAB0 MIFko.cp75 as compared to the same antibody produced in the wildtype CHO-S cell line (FIGS. 11 and 11a).

Example 8

The above described examples 6 and 7 are repeated in an identical fashion, using a CHO cell line either stably expressing anti-MIF antibody 4 anti-MIF antibody RAB9 resulting in the production of anti-MIF antibody RAB4 or RAB9, respectively, and using a CHO cell line expressing anti-MIF antibody RAM4 or RAM9 or RAM0, resulting in the production of anti-MIF antibody RAM4, RAM9 or RAM0, respectively.

Example 9

Comparison of Antibody Productivity of MIF Wildtype and MIF Knockout Cell Lines Producing the Anti-MIF Antibody RAM0 in Shake Flask Fermentation RAM0MIFko.CHO-S.33 cp75 and the parenteral production cell line RAM0.CHO-S.33 showed highest expression level and cell viability at 28° C. In this experiment, both cell lines were grown in shake flasks at 37° C. to a cell density of approximately $3 \times 10^5$, incubated at 37° C. for one day and then shifted to 28° C. for another 19 days. Cell counts and viability were monitored using a CEDEX. Production of RAM0 was quantitated by a MIF specific binding ELISA.

The experiment showed the following results (data not shown)

Cells are highly viable over a long period of time

Cells stop growing at 28° C.

Cells continuously produce the antibody

The MIFko cell line very surprisingly shows essentially the same characteristics as the parenteral MIFwt cell line.

Example 10

Comparison of Antibody Productivity of MIF Wildtype and MIF Knockout Cell Line Producing the Anti-MIF Antibody 9 in a 3 Liter Scale Batch Fermentation Anti-MIF antibody RAM9 was produced in a CHO-DG44 cell line RAM9.CHO-DG44#20, containing the wildtype MIF gene and RAM9.CHO-DG44.MIFko#10 containing the knocked out MIF gene.

It was surprisingly shown, that similar levels of cell growth and productivity can be reached in both cell lines (data not shown).

The invention claimed is:

1. A method for the detection of Chinese hamster ovary (CHO)-macrophage migration inhibitory factor (MIF) contaminations in a monoclonal anti-MIF antibody preparation, the method comprising:
   i) contacting the anti-MIF antibody preparation with a polyclonal anti-CHO-MIF antibody, affinity purified against CHO-MIF, and
   ii) detecting the presence of CHO-MIF.

2. The method of claim 1 wherein the CHO-MIF contaminates a final CHO cell produced monoclonal anti-MIF antibody —preparation or a preparation of antigen-binding fragments thereof.

3. The method of claim 1 wherein the CHO-MIF is endogenous CHO-MIF produced by CHO cells.

4. The method of claim 1 wherein the detection is carried out by a semi-quantitative Western Blot analysis.

5. A method for detecting CHO-MIF contaminations in a preparation during production of monoclonal anti-MIF antibodies or antigen-binding fragments thereof or in the final preparation of monoclonal anti-MIF antibody or antigen-binding fragments thereof, the method comprising:
   i) contacting the monoclonal anti-MIF antibodies or antigen-binding fragments thereof containing preparation with a rabbit anti-CHO-MIF antibody, affinity purified against CHO-MIF, and
   ii) detecting the presence of CHO-MIF in the preparation.

6. The method of claim 5 wherein the detecting is carried out as a semi-quantitative Western Blot analysis.

7. A method for the production of anti-macrophage migration inhibitory factor (MIF) antibodies or antigen-binding fragments thereof in Chinese hamster ovary (CHO) cells, wherein the method comprises:
   i) producing the anti-MIF antibodies or fragments thereof in a cell culture supernatant,
   ii) contacting the cell culture supernatant with a polyclonal anti-CHO-MIF antibody, affinity purified against CHO-MIF, and
   iii) detecting the presence of CHO-MIF in the cell culture supernatant.

8. A method for producing a recombinant human macrophage migration inhibitory factor (MIF) antibody preparation, the method comprising;
   expressing the recombinant human MIF antibody in a Chinese hamster ovary (CHO) cell line,
   ii) contacting the preparation with a polyclonal anti-CHO-MIF antibody, affinity purified against CHO-MIF, and
   iii) detecting the presence of CHO-MIF.

9. The method of claim 8 wherein the amount of the CHO-MIF detected is below 0.5 ppm.

10. The method of claim 8, wherein the recombinant human macrophage MIF antibody is selected from the group consisting of:

i. a RAB9 antibody, characterized by a light chain sequence as deposited by way of plasmid deposition with deposit number DSM 25111 and a heavy chain sequence as deposited by way of plasmid deposition with deposit number DSM 25113, ii. a RAB4 antibody, characterized by a light chain sequence as deposited by way of plasmid deposition with deposit number DSM 25110 and a heavy chain sequence as deposited by way of plasmid deposition with deposit number DSM 25112, iii. a RAB0 antibody, characterized by a light chain sequence as deposited by way of plasmid deposition with deposit number DSM 25114 and a heavy chain sequence as deposited by way of plasmid deposition with deposit number DSM 25115, iv. a RAM9 antibody, characterized by a light chain sequence as deposited by way of plasmid deposition with deposit number DSM 25859 and a heavy chain sequence as deposited by way of plasmid deposition with deposit number DSM 25860, v. a RAM4 antibody, characterized by a light chain sequence as deposited by way of plasmid deposition with deposit number DSM 25861 and a heavy chain sequence as deposited by way of plasmid deposition with deposit number DSM 25862, vi. a RAM0 antibody, characterized by a light chain sequence as deposited by way of plasmid deposition with deposit number DSM 25863 and a heavy chain sequence as deposited by way of plasmid deposition with deposit number DSM 25864, vii. a RAB9 antibody, which is characterized by a light chain amino acid sequence of SEQ ID NO:22 and a heavy chain amino acid sequence of SEQ ID NO:26, viii. a RAB4 antibody, which is characterized by a light chain amino acid sequence of SEQ ID NO:23 and a heavy chain amino acid sequence of SEQ ID NO:27, ix. a RAB0 antibody, which is characterized by a light chain amino acid sequence of SEQ ID NO:24 and a heavy chain amino acid sequence of SEQ ID NO:28, x. a RAM9 antibody, which is characterized by a light chain amino acid sequence of SEQ ID NO:33 and a heavy chain amino acid sequence of SEQ ID NO:32, xi. a RAM4 antibody, which is characterized by a light chain amino acid sequence of SEQ ID NO:35 and a heavy chain amino acid sequence of SEQ ID NO:34, and xii. a RAM0 antibody, which is characterized by a light chain amino acid sequence of SEQ ID NO:31 and a heavy chain amino acid sequence of SEQ ID NO:30.

11. The method of claim 1 wherein the amount of the CHO-MIF is below 0.5 ppm.

12. The method of claim 11 wherein the amount of the CHO-MIF is below 0.2 ppm.

13. The method of claim 5 wherein the amount of the CHO-MIF is below 0.5 ppm.

14. The method of claim 13 wherein the amount of the CHO-MIF is below 0.2 ppm.

15. The method of claim 7 wherein the amount of the CHO-MIF is below 0.5 ppm.

16. The method of claim 15 wherein the amount of the CHO-MIF is below 0.2 ppm.

17. The method of claim 9 wherein the amount of the CHO-MIF is below 0.2 ppm.

18. The method of claim 10 wherein the recombinant human macrophage MIF antibody is a RAB9 antibody, characterized by a light chain sequence as deposited by way of plasmid deposition with deposit number DSM 25111 and a heavy chain sequence as deposited by way of plasmid deposition with deposit number DSM 25113.

19. The method of claim 10 wherein the recombinant human macrophage MIF antibody is a RAB4 antibody, characterized by a light chain sequence as deposited by way of plasmid deposition with deposit number DSM 25110 and a heavy chain sequence as deposited by way of plasmid deposition with deposit number DSM 25112.

20. The method of claim 10 wherein the recombinant human macrophage MIF antibody is a RAB0 antibody, characterized by a light chain sequence as deposited by way of plasmid deposition with deposit number DSM 25114 and a heavy chain sequence as deposited by way of plasmid deposition with deposit number DSM 25115.

21. The method of claim 10 wherein the recombinant human macrophage MIF antibody is a RAM9 antibody, characterized by a light chain sequence as deposited by way of plasmid deposition with deposit number DSM 25859 and a heavy chain sequence as deposited by way of plasmid deposition with deposit number DSM 25860.

22. The method of claim 10 wherein the recombinant human macrophage MIF antibody is a RAM4 antibody, characterized by a light chain sequence as deposited by way of plasmid deposition with deposit number DSM 25861 and a heavy chain sequence as deposited by way of plasmid deposition with deposit number DSM 25862.

23. The method of claim 10 wherein the recombinant human macrophage MIF antibody is a RAM0 antibody, characterized by a light chain sequence as deposited by way of plasmid deposition with deposit number DSM 25863 and a heavy chain sequence as deposited by way of plasmid deposition with deposit number DSM 25864.

24. The method of claim 10 wherein the recombinant human macrophage MIF antibody is a RAB9 antibody, which is characterized by a light chain amino acid sequence of SEQ ID NO:22 and a heavy chain amino acid sequence of SEQ ID NO:26.

25. The method of claim 10 wherein the recombinant human macrophage MIF antibody is a RAB4 antibody, which is characterized by a light chain amino acid sequence of SEQ ID NO:23 and a heavy chain amino acid sequence of SEQ ID NO:27.

26. The method of claim 10 wherein the recombinant human macrophage MIF antibody is a RAB0 antibody, which is characterized by a light chain amino acid sequence of SEQ ID NO:24 and a heavy chain amino acid sequence of SEQ ID NO:28.

27. The method of claim 10 wherein the recombinant human macrophage MIF antibody is a RAM9 antibody, which is characterized by a light chain amino acid sequence of SEQ ID NO:33 and a heavy chain amino acid sequence of SEQ ID NO:32.

28. The method of claim 10 wherein the recombinant human macrophage MIF antibody is a RAM4 antibody, which is characterized by a light chain amino acid sequence of SEQ ID NO:35 and a heavy chain amino acid sequence of SEQ ID NO:34.

29. The method of claim 10 wherein the recombinant human macrophage MIF antibody is a RAM0 antibody, which is characterized by a light chain amino acid sequence of SEQ ID NO:31 and a heavy chain amino acid sequence of SEQ ID NO:30.

* * * * *

UNITED STATES PATENT AND TRADEMARK OFFICE
CERTIFICATE OF CORRECTION

PATENT NO. : 9,465,037 B2  
APPLICATION NO. : 14/350187  
DATED : October 11, 2016  
INVENTOR(S) : Randolf J. Kerschbaumer et al.

Page 1 of 1

It is certified that error appears in the above-identified patent and that said Letters Patent is hereby corrected as shown below:

On the Title Page

Item [54], delete "CHARACTERIZATION OF CHO-MIF GENE AND PROTEIN, AND USE THEREOF" and insert therefor -- METHODS FOR DETECTING AND PRODUCING MACROPHAGE MIGRATION INHIBITORY FACTOR (MIF) --.

Item [71], delete "Baxalta GmbH, Glattpark (Opfikon) (CH); Baxalta Incorporated, Bannockburn, IL (US)" and insert therefor -- Baxalta Incorporated, Bannockburn, IL (US); Baxalta GmbH, Glattpark (Opfikon) (CH) --.

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*